United States Patent
Singh

(10) Patent No.: US 10,040,463 B2
(45) Date of Patent: Aug. 7, 2018

(54) RAILROAD TRACK SURVEY SYSTEM

(71) Applicant: Sameer Singh, Castle Donington (GB)

(72) Inventor: Sameer Singh, Castle Donington (GB)

(*) Notice: Subject to any disclaimer, the term of this patent is extended or adjusted under 35 U.S.C. 154(b) by 203 days.

(21) Appl. No.: 14/982,312

(22) Filed: Dec. 29, 2015

(65) Prior Publication Data

US 2017/0106885 A1    Apr. 20, 2017

(30) Foreign Application Priority Data

Oct. 20, 2015 (GB) .................................. 1518599.4

(51) Int. Cl.
| | |
|---|---|
| *G06F 11/30* | (2006.01) |
| *B61L 23/04* | (2006.01) |
| *B61L 25/02* | (2006.01) |
| *G01B 11/22* | (2006.01) |
| *G01N 21/88* | (2006.01) |

(52) U.S. Cl.
CPC ........... *B61L 23/042* (2013.01); *B61L 23/045* (2013.01); *B61L 25/021* (2013.01); *B61L 25/023* (2013.01); *B61L 25/025* (2013.01); *G01B 11/22* (2013.01); *G01N 21/8851* (2013.01); *B61L 2205/04* (2013.01); *G01N 2201/10* (2013.01); *G01N 2201/12* (2013.01)

(58) Field of Classification Search
CPC ......... G01T 1/167; G01T 7/00; G01V 5/0025; G01V 5/0016; G01V 5/005; G01V 5/0083; G06T 7/12; G06T 17/20; G06T 2207/10016; G06T 2207/10048; G06T 2207/10088; G06T 2207/20116; G06T 2207/30016

See application file for complete search history.

(56) References Cited

U.S. PATENT DOCUMENTS

| | | |
|---|---|---|
| 9,049,433 B1 | 6/2015 | Prince |
| 2011/0064273 A1 | 3/2011 | Zarembski et al. |
| 2012/0192756 A1 | 8/2012 | Miller et al. |
| 2012/0263342 A1 | 10/2012 | Haas et al. |

(Continued)

FOREIGN PATENT DOCUMENTS

EP    1236634 A1    9/2002

OTHER PUBLICATIONS

European Search Report in related European Application No. 16 18 5039, dated Jan. 18, 2017, 2 pages.

(Continued)

*Primary Examiner* — Robert Bachner
(74) *Attorney, Agent, or Firm* — Law Office of Jeff Williams; J. Oliver Williams

(57) ABSTRACT

The present application involves a railroad track inspection system comprising a plurality of track scanning sensors, a data store, and a scan data processor. The data store is used for storing track scan data recorded by the track scanning sensors. The scan data processor is used for automatic analysis of the track scan data upon receipt thereof to detect one or more track components within the scan data from a predetermined list of component types according to one or more features identified in said scan data. The system comprises a common support structure to which the track scanning sensors, the data store and scan data processor are attached, the common support structure having a mounting for attachment of the system to a railway vehicle in use.

54 Claims, 9 Drawing Sheets

(56) References Cited

U.S. PATENT DOCUMENTS

| | | |
|---|---|---|
| 2012/0274772 A1 | 11/2012 | Fosburgh |
| 2013/0096739 A1 | 4/2013 | Landes et al. |
| 2013/0191070 A1* | 7/2013 | Kainer .................... B61K 9/08 |
| | | 702/167 |
| 2015/0201165 A1 | 7/2015 | Bocionek |

OTHER PUBLICATIONS

United Kingdom Intellectual Property Office Search Report in related UK application No. GB1515648.2, dated Feb. 11, 2016, 4 pages.
Office Action in related U.S. Appl. No. 14/982,212.

\* cited by examiner

RAILROAD TRACK SURVEY SYSTEM

BACKGROUND

1. Field of the Invention

The present invention relates to apparatus for the surveying of railroad track, and more particularly, although not exclusively, apparatus for assessing track health based on inspection.

2. Description of Related Art

Railroad tracks, also known as 'permanent way', consist of rails, fasteners, sleepers (ties), ballast and the underlying subgrade. A wide variety of variations are possible in terms of types of rail used, jointed or continuous welded, use of sleepers with ballast or slab track, type of fastenings used, and switch layouts. A number of associated track assets are also mounted on conventional railroad, such as equipment of signaling, lubrication, cabling and/or switch operation, amongst others. Over time, track components and assets degrade and endure damage because of the physical stress caused by movement of trains, changes in weather conditions causing compression or expansion in materials, rain and environmental conditions, and degradation in material strength with age.

Railroad track inspection processes are aimed at finding missing and defective components so as to be able to carry out effective maintenance with the intent of repair or replacement. If the track and associated assets are not monitored effectively, then there is a risk of complete failure or degradation to the extent that a significant risk is posed to safe operation of the railroad.

Human track inspectors have conventionally carried out the job of visual track inspection by walking along the railway track and taking notes on track condition which is later used to guide track maintenance activities. Such form of inspection is costly, unsafe, slow and prone to human error. Growth in rail networks, coupled with the time required for manual inspection has made it difficult in practice to carry out manual track inspection at the required inspection frequency with full network coverage.

Over the last two decades, rail infrastructure operators have increasingly started to carry out track monitoring using dedicated "inspection trains". These trains are designed for hosting equipment for semi or fully automated track inspection equipment. Currently available systems of this kind use scanning equipment, including cameras and/or laser scanners, for monitoring various parts of the track. Implementation of the systems on inspection trains results in the various system components being distributed over a local network for the system, with sensing equipment being typically mounted on the vehicle exterior and data storage and control systems being mounted with a cabin interior, e.g. within suitable racks.

The implementation and maintenance of such systems is costly, and time consuming. In particular, such systems need extensive configuration to fit to a given vehicle which increases the complexity of installation and future maintenance burden. Each inspection train thus requires customisation such that it is fit for purpose. The overall distributed architecture comprising hardware components both outside and inside the vehicle, high power consumption, and the permanent equipment fixtures arrangement means that inspection trains have developed with time as their own subtype of railway vehicle.

However the cost of running inspection trains is burdensome. Not only due to the aforementioned installation and maintenance costs, but also because of the need to schedule inspection train journeys along busy railway lines. The running of inspection trains is to the potential detriment of the railway line capacity for passenger or freight vehicles, particularly considering the relatively low speeds at which conventional inspection trains gather data.

The data produced by the track scanning process may be transferred to an off-site computer network, where it can be analysed. The requirement for data to be amassed and communicated to a central location for processing, coupled with the detailed processing of the recorded data, can lead to a significant delay between the inspection itself and the deduction of any action required based on the inspection. Furthermore it can be problematic handling the large volumes of scan data generated.

It is an object of the present invention to provide a railroad track surveying system that overcomes or substantially mitigates one or more of the above disadvantages associated with the prior art. It may be considered an additional or alternative aim of the invention to provide a system that can provide useful track inspection results in a more convenient manner.

Although great strides have been made, considerable shortcomings remain.

SUMMARY OF THE INVENTION

According to an aspect of the invention there is provided a railroad track inspection system comprising a plurality of track scanning sensors, a data store for storing track scan data recorded by the track scanning sensors, and a scan data processor for automatic analysis of said track scan data upon receipt thereof to detect one or more track components within the scan data from a predetermined list of component types according to one or more features identified in said scan data, wherein the system comprises a common support to which the track scanning sensors, the data store and scan data processor are attached, the common support having a mounting for attachment of the system to the exterior of a railway vehicle in use.

The common support may allow attachment of the system to a railroad vehicle as a unit, e.g. as a single fixture or assembly. The common support may comprise a housing, e.g. a rigid enclosure for the internal system elements, such that the system can be mounted to the railroad vehicle in the form of an enclosed module. The system may be fitted to new railway vehicle or retrofitted to existing vehicles in a simple manner, for example allowing the system to be used on passenger or freight vehicles, as well as inspection trains and other vehicle types. A single customised support/housing structure allows the internal system to be optimised for scan data processing such that track analysis can be performed in, or close to, real time.

The common support and/or housing may comprise a power and/or data connector for the system, i.e. to allow electrical power supply to the system and/or data communication between the system and the railroad vehicle and/or another network. A common power and/or data connector for the whole system may be provided. The system may comprise a data transmitter and/or receiver.

The scanning sensors may comprise one or more image capture sensor. The image capture sensor may comprise a light sensor, e.g. for capturing a visual image, such as a camera. One or more line scan sensor or area scan sensor may be used. Additionally or alternatively, the scanning sensors may comprise either or both of a laser scanner or thermal/infra-red image capture sensor.

The common support and/or housing may comprise one or more window arranged in the field of view between one or more sensor and the track to be scanned in use. A plurality of window portions may be arranged at different angular orientations. A plurality of window portions may be arranged at opposing angular, e.g. oblique, orientations. A central window portion may be arranged between the opposing window portions. The opposing window portions may be symmetrical about a central axis or plane, e.g. corresponding to the central axis of a rail in use.

The scan processor and/or data store may be provided as a removable processing unit or module, which may be releasably coupled, e.g. mechanically and electrically, to the common support and/or housing for use. The removable processing unit may comprise an enclosure in which the scan processor and/or data store is housed. The enclosure may comprise a data and/or power connector for connection with a corresponding connector on the common support. The removable processing unit may comprise a battery and/or transmitter/receiver circuitry.

The scan processor may construct an image of a length or section of track from a plurality of scans from one or more of the scanning sensors. The scan processor may concatenate a plurality of images from a single sensor (e.g. using consecutive scans) or a plurality of sensors.

The scan data may comprise digital image data, for example comprising pixel intensity values. The scan data may comprise a matrix of pixel data. The scan data may comprise a visual image and/or thermal image.

The scan data processor may identify pixel clusters within an image according to one or more pixel property, such as brightness or colour. Pixel clusters may be used to determine edge, colour, texture, shape and/or other statistical properties for an asset. A pixel cluster may represent an object, such as a track component or part thereof.

The one or more scan data feature may comprise a geometric and/or color feature. One or more shape/geometric feature of the track, or a component thereof, such as an edge or dimension, may be determined from one or more image capture sensor, e.g. according to colour and/or brightness/intensity within the captured data. Additionally or alternatively a geometric feature may be determined from a different scanning sensor such as a laser/distance sensor. A profile of a track component may be determined using a laser sensor, e.g. a profile of a rail.

The plurality of scanning sensors may comprise a plurality of the same or different types of image capture sensor. Different sensor types may comprise sensors for different electromagnetic radiation types/wavelengths. Alternatively different scanning sensor types may comprise different sensor dimensionality or orientation, e.g. such as area scan, line scan, depth detection sensors and/or three-dimensional surface scanning/imaging devices. Automatic track component classification and or status assessment may be beneficially improved by multiple track view analysis. The system may compare/contrast two-dimensional and three-dimensional scan data of one or more common track component in determining the component type and/or status.

One or more scanning sensor or other sensor type may be used for track component distance/spacing measurement.

Different sensor types may be used in parallel. For example, the output of each sensor may be used to detect/assess track components independently, e.g. using the same or a different type of assessment depending on sensor type. The scan data processor may receive the different sensor inputs and may use them in combination to determine a track component type and/or track component status. The combination of different modalities in this manner can provide greater certainty of automated track inspection, for example in which a finding using one modality is compared to a corresponding finding using another modality in order to confirm or reject that finding.

The system may comprise a plurality, e.g. three or more, track scanning sensors for each rail under inspection. First and second sensors may or may not be positioned on either side of the rail, e.g. as flanking sensors. The first and second and sensor may be laterally offset from the axis, e.g. on either side of the rail or a vertical axis/plane of the rail. The first and second sensors are typically obliquely angled, e.g. relative to an axis/plane of the rail.

One sensor, e.g. a third sensor, may be a central sensor, which may be positioned above the rail, e.g. directly/vertically above the rail. That sensor may be generally aligned with the vertical axis/plane of the rail, e.g. looking down thereon, so as to provide a plan view of the rail head.

The system may comprise first and second sets of sensors, each set of sensors being arranged to scan a single rail, wherein the common support comprises a common spacer or lateral support member to which each set of sensors is mounted, e.g. in a spaced arrangement and/or towards opposing ends of the common spacer. The common support may comprise a plurality of lateral beams.

Any or any combination of the track scanning sensor(s) may be adjustably mounted to the common support, e.g. to adjust the field of view of the image capture sensor(s). The sensor mountings may be individually or commonly adjustable. Lateral movement of any or any combination of the scanning sensors may be accommodated. Additionally or alternatively angular adjustment and/or focal length adjustment may be used. Additionally or alternatively adjustment of a lens and/or aperture may be used to adjust (e.g. widen/reduce) the sensor field of view. An angular or focal adjustment mechanism may be provided for each sensor or sensor type, e.g. individually, whereas a lateral movement mechanism may be provided collectively for the system or the plurality of sensors as a whole.

The common support may comprise an adjustable support structure, e.g. to allow adjustment of the position of the plurality of sensors and/or the system as a whole. The common support may allow position adjustment relative to the mounting. The common support may comprise a movable portion, such as a movable housing/enclosure, which is variably positionable relative to the mounting. The common support may allow common position adjustment for any combination or all of the plurality of scan sensors, e.g. to accommodate track curvature or the like.

Common position adjustment for the scanning sensors in use may be limited to a single degree of freedom, e.g. lateral adjustment relative to the direction of the rail(s) under inspection. Common position adjustment may be used to follow, i.e. dynamically, the direction of the railway track in use, e.g. by remaining aligned with one or both rail of the track.

The common support may comprise at least one rail or runner. A housing for one or more scanning sensor, e.g. a common housing, may be mounted to the runner.

The system may comprise an actuator for position adjustment relative to the mounting. The actuator may be arranged for linear/lateral actuation, e.g. by way of a linear actuator or a rotor comprising a mechanism for converting rotational/torque input to linear motion. The actuator may be electrically powered, such as an electro-mechanical actuator.

The common support may be adjustably mounted to accommodate height adjustment of the sensors and/or the system as a whole. Height adjustment may be implemented to attain a predetermined height above the track and/or a rail thereof. Height adjustment may be implemented dynamically during use of the sensors or may be set at a predetermined height prior to use. Height adjustment may allow alteration of the field of view of one or more scanning sensor. Height adjustment may be used to effect different modes of operation of the system, for example to include rail inspection or whole track inspection. Different heights may be suited to inspection of different specific track component types.

The system may comprise a controller, e.g. mounted on the common support and/or within a common housing. The controller may control any or any combination of: the track scanning sensors; power management for the system, e.g. including charging of one or more battery; thermal management of the system; data communications to/from the system, e.g. including alerts; lighting or other irradiation of the track for the scanning sensors. The controller functionality may be provided by one or more processor. The scan data processor may perform some or all controller functionality or else a separate system controller may be provided.

The rate of track scanning may be controlled according to the railroad vehicle travel speed. A predetermined rate of scan/image capture or volume of scan data per unit distance may be set. For example, a rate of pixel capture per mm distance along the track may be set. A pulsed signal at a pulse frequency according to vehicle speed may be used to control the scanning rate. Additionally or alternatively, the rate of track scanning may be altered according to user requirements and/or predetermined track sections, e.g. according to different modes of track scanning.

A vehicle wheel or drive shaft tachometer may be used to determine travel distance/speed. A laser Doppler device may be used.

The system may comprise an irradiation/light source. A dedicated light source mounted on the common support may provide bespoke illumination for the purpose of the invention. A linear light source array (e.g. a linear array of LED's) may extend across the width of the common support and/or track in order to provide uniform lighting across the track section being scanned. The light source may be operated in a discontinuous, e.g. pulsed or intermittent, manner. The light source may or may not be pulsed according to the scan frequency of one or more sensors and/or vehicle speed.

One or more scan sensor may comprise a filter, e.g. a light filter. The filter may be adapted to prevent unwanted wavelengths within the scan data and may for example be tailored to a light source of the system. The operation of the system may adjust according to the level of the light received by the sensors. An aperture or filter of the/each scanning sensor may be adjustable, e.g. according to the ambient light level.

The system may comprise a location determination device/system. The track scan data recorded by the sensors may be logged with a location record (e.g. a geographical location record) from the location determination system. The location record may correspond to the sensor/vehicle location. Where a plurality of sensors are used the corresponding scan data captured by the plurality of sensors may be logged with a common location record.

The location record may comprise a plurality of components (e.g. latitude and longitude) according to a geographic coordinate system. The location record may additionally or alternatively comprise a local or relative coordinate value, e.g. relative to the railroad track. The location record may comprise a one-dimensional location record component or value, e.g. according to distance along the railroad from a datum point. In any examples, the location record may be supplemented with, or substituted for, a time record (e.g. a timestamp).

The location determination system may comprise a vehicle travel distance sensor, such as a tachometer, and/or a track position sensor. This may be used in addition to, or instead of, a GPS or other geographic location system. Combining multiple location determination systems/sensor types may be used to increase the accuracy of track component location determination. A track position sensor may comprise a sensor for identifying track features indicative of known/predetermined track locations, e.g. fixed datum locations. One or more scanning sensor could be used for this purpose or else a near-field wireless communication transmitter receiver. An RFID sensor, for example, could be used to detect RFID tags mounted on the track at known locations. A lookup table of known tag locations may be used to determine asset and/or image sensor location.

The system may comprise a thermal management device, e.g. a cooling and/or heating device. A fan, peltier air cooler or liquid cooling system may be used. A common housing may comprise one or more vents to permit airflow through the housing interior.

The system may comprise a local power source, such as a battery. The local power source may allow at least some functions of the system to operate in isolation of an external power connection. For example, the battery may allow processing of received scan data, e.g. in order to complete scan data analysis after power supplied by the railroad vehicle has been cut off. The local power source may be charged by vehicle motion, e.g. vibration and/or wheel motion.

The scan data processor may comprise a plurality of processors/chips, wherein at least one processor is arranged to log captured scans/images and associated location data in real time in the data store. Said processor may be arranged to collate image/scan and/or associated data from a plurality of sensors/sources.

At least one processor may be arranged to process the captured scan data to identify tack components substantially in real-time or with a slight time delay, e.g. near-real time. At least one processor may be arranged to perform image analytics on images captured by the scan sensor(s). Scan data may be logged in parallel with analytical processing thereof. A central controller may determine which of the processes are carried out concurrently according to data input rate and/or processing rate. Any or any combination of the processors may operate automatically upon receipt of the relevant data.

Scan data storage may comprise indexing scan data with a location and/or time data record. Scan data storage may comprise storing scan data as a flat (e.g. binary) pixel data format, or as compressed images with conventional formats such as JPEG, e.g. with a location identifier. For flat file format, scan data file header information may be added at a subsequent processing stage (e.g. not in real-time or near real-time).

At least one scan data processor may be arranged to process the recorded scan data so as to analyse track component status either on board the common support structure, on board the railway vehicle, or else at a remote location, e.g. at a time after scan data acquisition. The system may output track component identification, location and/or status in real-time, e.g. such that there is substantially no delay or negligible delay between when the track components are visible within the field of view of the scanning sensors, and their detection by the automated scan data analysing system. This allows for the operator to view track component identification and/or status as the vehicle passes those components in real-time. The scan processor may output track component status either immediately or with a relatively short time delay after image capture, e.g. in near real-time. In any example of the invention the recorded scan data processing time may comprise a relatively shorter time period or speed compared to the travel time or speed of the vehicle, such as for example a fraction of the travel time/speed, e.g. less than a half or quarter of the vehicle travel time/speed, or an order of magnitude or more less than the vehicle travel time/speed, at normal vehicle speeds. In case of near real-time, there is a short delay between when the sensors are able to view a track component, and when it is registered as found with its measured properties within a database used by the scan data processor. This delay can be variable based on the hardware capability and complexity of scan data analysis software.

The data store may comprise a processed scan/image data store and a buffer. The processed scan data store may comprise scan image files and associated track component classification and/or status data. Real-time or immediate processing of data as referred to herein may occur at the rate of scan data acquisition, e.g. substantially avoiding use of the buffer. The processed scan/image data store may comprise location data corresponding to the stored images.

The scan data processor may comprise a central processor and either or both of a field programmable gate array and a graphics card. The ability to divide up the processing between different processors is beneficial in defining a hierarchy of processing tasks.

The scan data processor may comprise a sensor data collation/management module and data analysis module. A more detailed data review module may be provided as part of the system but may be only selectively employed by a central processor. A modular approach to data processing may allow a different combination tasks to be performed selectively for different track assessment jobs. Not all tasks need be performed for all uses of the system. For example, some processing stages can take precedence and always be performed (e.g. in real time), such as scan data indexing, whilst one or more further data analysis stage may be optionally employed.

Dimension and/or shape measurement of track components may be matched to predetermined shape profiles. One, two or three dimensional shape model constructs and/or analysis may be used.

A confidence score may be determined for, and/or assigned to, a track component determination by the system according to a degree of the match between one or more geometric feature/profile and/or surface property feature of a track component identified in the recorded track scan data and one or more predetermined component features. It has been found that the combination of shape matching and colour/texture matching yields improved certainty in component identification and condition analysis.

The system may comprise a plurality of track component detector, e.g. different types of classifier. One classifier may or may not comprise a rule-based classifier, e.g. employing statistical and/or semantic rules for component matching. One asset classifier may or may not comprise a template classifier, e.g. matching a component shape/surface property using one or more correlation-based matching method, such as a neural network or genetic algorithm. One component classifier may or may not comprise a feature matching tool, e.g. by which pixel clusters are statistically matched to component attributes/features in predetermined component recognition tables.

Template matching may be used for track component detection/identification. The list of predetermined component types may comprise a list of predetermined component templates. Predetermined templates may comprise one or more geometric feature and/or one or more surface property feature. Geometric template features may comprise curvature, edge and/or dimension features. Surface property features may comprise colour, brightness/intensity, and/or surface uniformity/variation.

A location determining system for images captured by the sensor and an image processor, the image processor comprising an asset classifier for detecting an asset in one or more captured image and classifying the detected asset by assigning an asset type to the detected asset from a predetermined list of asset types according to one or more feature in the captured image, and an asset status analyser for identifying an asset status characteristic and comparing the identified status characteristic to a predetermined asset characteristic so as to evaluate a deviation therefrom.

The scan data processor may serve as a novelty/anomaly detector. In the event that the processor identifies a detected component/feature that does not meet criteria for assigning a predetermined track component type, the asset classifier may log an instance of novel object detection. The scan data processor may log any or any combination of: scans/images in which the unrecognised object is identifiable; a location of the unidentified object; processed scan data (such as surface property and/or profile) for the unidentified object. This log may be later analysed to create a new component type or assign an existing component type to the object.

An alert module may be provided, which may receive the output of the scan data processing and determine whether one or more alert condition is met. Alert criteria may be set based on component type/status and/or novelty/anomaly detection. Semantic knowledge comparison may be performed prior to alert output, e.g. to avoid false positives, for at least some component types.

The scan data processor may be accompanied by additional hardware responsible for image or laser data compression. In some cases, the sensor modules may have a built-in module for data compression or performing a limited set of analytics.

The scan data processor may perform track component change analysis. The scan data processor may compare current scan data with prior scan data at the same location or a previously determined component status characteristic, e.g. a geometric or surface characteristic. Changes in track component orientation, shape, edge and/or colour may be monitored. The system may log changes/deterioration of track components, both instantaneously (i.e. between two successive passes of the component) and/or over extended periods of time, such as days, weeks, months, years. Depending on data storage capability, one or more status characteristics may be logged for comparison with later determined status characteristics. Comparison of simple asset status characteristic values may avoid the need to re-process previously logged image data. Previously logged component status characteristics may be stored in the scan data store or another on-board data store, for comparison in real-time or near real-time.

According to a second aspect of the invention, there is provided a railroad track inspection method corresponding to use of the system of the first aspect.

According to a further aspect of the invention there is provided a data carrier comprising machine readable code of the operation of a track scan data processor in accordance with the system or method of the above aspects.

Any of the optional features defined above in relation to the first aspect of the invention may be applied to any further aspect.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

Figure 1:
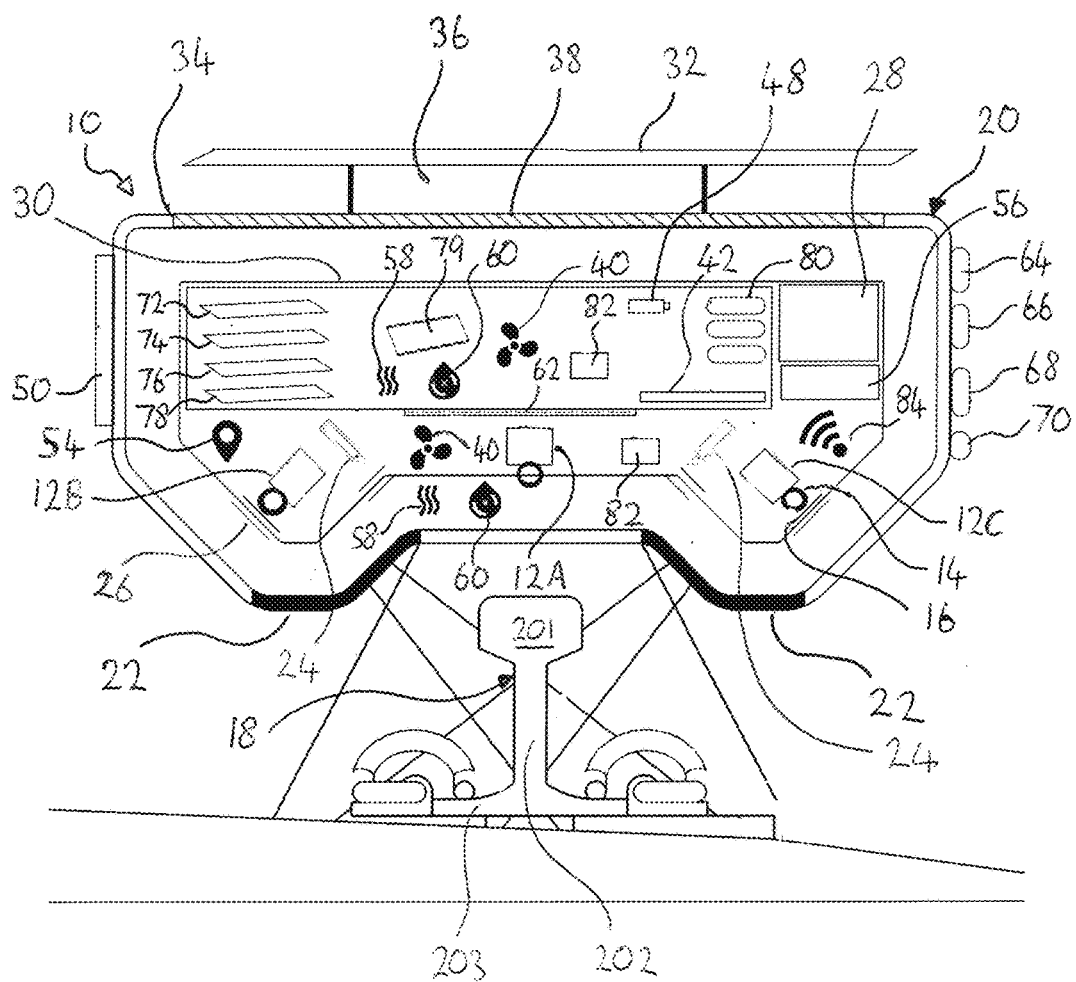
FIG. 1 shows a schematic section view through a housed rail track inspection system according to an example of the invention.

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Examples of the invention described hereinbelow concern the use of a housed system for surveying railroad track, herein termed a "TrackVue" system. All the equipment required for scanning, processing and logging the visual and/or geometric features of railroad track are provided with a common support structure so as to allow for a system that can be installed on passenger trains and/or freight trains as well as, or instead of, being installed on dedicated inspection vehicles. A singular housed unit or installation of this kind is well suited for retrofitting on existing trains and can offer simple installation and operation. Systems according to examples of the invention may provide so-called 'plug-and-play' functionality when compared to the systems used in the prior art.

Turning firstly to FIG. 1, the system 10 includes a plurality of track scanning sensors, which in this example comprise a plurality of imaging sensors 12. The imaging sensors are preferably capable of recording electromagnetic radiation in the visible range, i.e. visible light, but may additionally encompass infrared wavelengths. In some examples of the invention, thermal imaging may also be accommodated. Both visible and thermal radiation wavelengths may be sensed at once by a common sensor and subsequently filtered to separate the visible and thermal/infrared images. Alternatively, different individual sensors may be mounted at one or more imaging sensor unit 12 with physical filters to control the wavelengths of radiation detected by each sensor. In either example, separate thermal/infrared (IR) and visible light images can be recorded. In other examples, it is possible to additionally or alternatively use near-IR sensors/filters.

The system may use x-rays for imaging the internals of a rail or surrounding components. The object to be imaged is positioned in between an x-ray source and a linescan x-ray scanner. The power of the source is sufficient to generate x-rays that can penetrate the rail or other components and the transmitted x-rays are sensed by the linescan sensor on the other side of the object. The resulting images can be processed for recognising internal cracks, air gaps and other defects.

The number and configuration of imaging sensors placed can be tailored to cover the entirety of the railroad track, as will be discussed in further detail below, or just specific portions thereof as required. The key properties of each imaging sensor comprise any or any combination of: whether it is color or monochrome; horizontal and vertical image resolution; scanning frequency in hertz; the type of interface with image acquisition devices including GIGE, CAMLINK, USB, etc.; sensor type and size; and, any inbuilt intelligence to perform analysis, data compression or dynamic adjustment of its imaging parameters to cater to changes in the environment. The sensors can be chosen to suit the environment for imaging on a mainline passenger, freight, metro, underground or dedicated inspection train, as well as on rail-adapted vehicles (e.g. hy-rail) and trolley-based platforms such that their imaging sensors can cover the overall area of survey and inspection as desired for a particular application.

Each imaging sensor 12 in this example comprises a lens 14 and filter 16. The lenses 12 can be of fixed or variable focal length and define the field of view required for image capture. Appropriate cut-off filters 16 can be provided so as to limit the range of electromagnetic wavelength to which the sensor is exposed in use. This may reduce the external light interference from certain wavelengths.

In the example shown in FIG. 1, three imaging sensors 12 are shown. A central imaging sensor 12A is positioned generally about a rail 18 to be inspected in use, and two flanking imaging sensors 12B and 12C are positioned on either side thereof. The central sensor 12A provides an above view, i.e. a plan view, of a rail 18 in use, whereas the flanking 12B and 12C sensors are obliquely angled relative thereto and provide a view of the remainder of the track to each side of the rail. The angular offset between the sensors 12 is substantially in a common/vertical plane. The angular offset of the sensors 12B and 12C may be roughly 45° off the axis of alignment of sensor 12A, although the offset may be adjusted according to the field of view by virtue of lens 14 and so may encompass wider or narrower oblique angular offset.

The fields of view of the sensors 12 may be overlapping to ensure full coverage. In this regard, it will be appreciated that the arrangement of FIG. 1 is for scanning a single rail 18 including the flanking railroad track portions on either side of that rail, and that a further complement of sensors is provided for the adjacent rail. Only a single set of sensors is described for conciseness and it is assumed that the further set of sensors for the adjacent rail will match the sensors described in relation to FIG. 1. The different fields of view collectively cover the entire width of the railroad track from one end of each sleeper to the opposing end. Thus imaging is performed for the track region on either side of the rails, e.g. with the option of sleeper ends, and not just the rails themselves.

In the example of FIG. 1, the imaging sensors 12 are digital scanners/cameras in the form of linescan sensors. The linescan imaging sensors 12 thus have a narrow/linear field of view arranged laterally across the railroad track in use, i.e. relative to the direction of the track or a longitudinal axis thereof. Scanning a sequence of narrow lines in this manner allows a collection of lines to be built up and concatenated to form an image. The number of pixels in one linear scan is determined by the imaging sensor resolution. In other examples of the invention, it will be appreciated that area scan imaging sensors could be used in addition to, or instead of, the linescan sensors described above.

A suitable imaging sensor 12 can be color or monochrome (grayscale).

The field of view of the imaging sensors comprises the track directly beneath the system 10, i.e. beneath the railroad vehicle to which the system is mounted. Thus the system has a top down view of the track. The field of view of each sensor could be modified by altering the lens position 14 if required. The recorded track image is thus a digital representation of the light reflected from the various track components in the scene, having a pixel density according to the resolution of the imaging sensors being used.

For a thermal imaging sensor, which may comprise a suitable thermal camera or a thermopile array, a digital image representing the heat sensed is recorded. The temperature values recorded are translated into an image representation that depicts the change in temperature across the scene, e.g. which could be output on a visual display to a human user, and is suitable for automated image analytics. The output of each of thermal and visible light sensors is therefore a sequence of images/frames, each comprising an ordered array of pixels covering the area of interest, each pixel having an associated color, brightness and/or heat energy (temperature) value.

The TrackVue system allows for adjustment the imaging sensor operation parameters, e.g. dynamically or through applied software control, such as aperture, exposure and gain settings in response to the amount of light detected by its internal sensor, thereby allowing for the recording of better quality images to compensate for any illumination changes over the imaged area. The system allows for adjustment of the sensor operation substantially in real time according to ambient changes in light levels by use of a suitable controller as will be described in further detail below.

The TrackVue system 10 includes a dedicated light source for illuminating the region of the track being scanned. This may be achieved by continuous illumination of an area of the track that is in the imaging sensors 12 field of view or else by pulsing/flashing the light source only when an image is being captured. FIG. 1 illustrates the position of high intensity LED lights 22 that are suitable for this purpose. The lights are integrated within the overall system assembly housing 20 such that they are mounted relative to said housing 20 and are powered via the system as will be described below. The light source may be provided as one or more strips of individual lights, e.g. corresponding to the image captured from the linescan sensor. The lights can be selected for specific wavelengths or can be pure white so as to enhance the quality of imaged objects in digital images.

The output of the light source is typically sufficient to provide the required lighting for operation in the absence of ambient/natural light. The sensor aperture, exposure and/or gain parameters may be used to substantially remove ambient effects on the sensor readings.

In addition to the digital imaging sensors 12, the example of FIG. 1 comprises one or more laser device 24 for use in obtaining a further source of sensor data for use in surveying the railroad track. In this example two laser devices 24 are provided for each rail 18. Each laser device 24 may be laterally offset from a central axis of the rail 18 and may be obliquely angled relative to vertical so as to image a side of the rail 18 as well as a portion of the rail head.

A suitable laser scanning system may comprise either a laser emitting device 24 on its own, or a laser device 24 having its own imaging/scanning sensor assembly. The laser-sensor data acquisition/processing components could be integrated with dedicated sensors within the laser device 24 itself, in a separate dedicated unit, or could be comprised within track imaging sensors 12 as shown in FIG. 1. In any example, the laser emitting device 24 (i.e. the laserhead) is commonly mounted with, and contained within, the overall system housing 20 and is powered thereby.

Each laser device 24 emits a narrow beam of laser on the object of interest for surface topology measurement. The laser thus forms a region of irradiation, i.e. a linear path or a region across the rail and the adjacent track components, the reflection of which is detected by the corresponding sensor so as to interpret the corresponding geometry of the reflecting surface(s). Thus a linear section or a wider area of the rail and any adjacent track components can be scanned, depending on the laser system implemented.

The length, width and orientation of the laser beam pattern can be modified to suit specific applications. The power of the laser is optimised to generate a beam that shows sufficient contrast between where it falls on the track, and its immediate surrounding areas.

The imaging sensors used for laser beam imaging can be configured to generate coordinate data for the beam position within a field of view, e.g. binary data comprising horizontal (x), vertical (y) and depth (z), and/or generate a two dimensional grayscale image showing the laser beam against its surroundings which provides a reference to the identity of the object under measurement. A grayscale image requires further processing to generate depth data for each point on the laser beam within the image with supplementary processing of background image to understand the identity of assets overlaid by the laser beam.

Dedicated laser imaging sensors for use with devices 24 could use area scan imaging at high frame rates and can be pulsed along with lasers. Pulsing as an option can be set in control circuitry either contained within assembly or a further control unit for the system as will be described below. Pulsing may serve to reduce laser emission, reduce overall power consumption and keep the lasers cooler than possible with constant emission.

Based on the above description, it will be appreciated that the scanning of railroad track may accommodate any, or any combination, of visible light (camera), depth (e.g. laser) and/or thermal scanning sensors, any of which may output image or surface profile/coordinate data to be used in the surveying system. Whilst the examples described herein comprise a full complement of imaging sensors, it is intended in examples of the invention, that individual sensors or sensor types will be selectively operable, such that not all sensors are required to be operable at all times. One or more sensor may be triggered for operation at only selected times, or for only certain types of asset inspection, whilst one or more other sensor may be always used. The system is designed such that the laser light source does not contaminate the readings taken by the other sensors and thus does not interfere with linescan and/or thermal imaging.

In FIG. 1 there is also shown an example of the image processing and ancillary equipment for operation of the track surveying system, mounted within common housing 20. The overall system is broadly split into three separate compartments/modules that are provided together a single unit for installation on a train. These are: (a) The main housing 20 of the TrackVue enclosure that houses sensors, lighting and other ancillary components; (b) A removable processing unit (RPU) 30 that is mechanically and electrically coupled to/within the main housing 20 for use and consists of data processing, storage and control hardware; (c) A battery 28 that also integrates with the main housing 20 to allow for system operation in addition to the use of power supplied via the railroad vehicle.

The main housing 20 defines a hollow enclosure to which any of the aforementioned scanning equipment 12A, 12B, 12C, 24 and any associated lighting 22 can be mounted. Corresponding openings/windows are provided in the housing 20 to allow imaging of the track components externally of the enclosure 20. The internal mounts for the scanning equipment within main housing enclosure may be adjustable, if needed, to allow for change in their viewing angles of the imaging sensors. Motorised/electrical angular adjustment mechanisms may be integrated into the camera/sensor mounts. This may be in addition to or instead of the sensor actuation equipment discussed in further detail below in relation to FIG. 2.

Each scan sensor and/or laser device 24 is typically placed behind a transparent window 26 which protects the sensor from the outside environment. The windows 26 are mounted in the wall of a common enclosure 20. A toughened glass or other suitably transparent material may be used for the window.

The shape of the housing enclosure 20 in this example is such that it provides adequate clearance from the rail 18, whilst also offering the required field of view for each scan sensor. Therefore a contoured form for the housing 20 has been determined as shown in FIG. 1 in which a central section of the housing wall (e.g. in the vicinity of the sensor 12A) is recessed relative to adjacent wall sections on each side thereof. Thus the housing provides on its underside a central inverted gulley, which is aligned with a rail 18 in use, e.g. with two 'lobes' or downwardly protruding housing portions on either side thereof. The windows provided in the enclosure 20 may thus comprise window portions at different angular orientations to accommodate the different viewing angles of the different scanning sensors and/or the orientation of the enclosure wall where the window is located.

The example of FIG. 1 shows a single enclosure 20 containing all the sensors required for scanning of a single rail and the surrounding track components. It will be appreciated that the overall system may comprise two sets of scanning equipment/sensors in respect of two rails to be scanned simultaneously. The system may thus comprise two or more enclosures or housing structures for each set of equipment, which may be provided as a commonly mounted structure to the railroad vehicle. Alternatively, the system could comprise a single enclosure spanning both rails. The ancillary equipment shown in FIG. 1 may all be accommodated in a single enclosure or split between a plurality of enclosures sharing a common mount to the vehicle as necessary.

The main housing 20 has a mount 32 for fixing the housing onto a railroad vehicle. In this example, the housing depends downwardly from an underside of a railroad vehicle and so upper wall 34 of the housing 20 has a mounting bracket 36 depending therefrom.

The cooling of the interior of both the main housing 20 and also the RPU 30 is an important operational consideration for dissipation of heat generated by the imaging sensors, laser, LED lights, as well as any computational equipment. The exterior of TrackVue housing 20 will be air cooled by motion of the train in use and so conductive cooling of any heat sources can be accommodated by thermally coupling the heat sources to the external wall of the housing 20. Depending on the design of the housing 20, the system may comprise one or more cooling device 38, e.g. including vents fins or the like, on the housing 20. Any such cooling device 38 may promote heat loss to the air flowing over the exterior of the housing 20 during motion of the railroad vehicle by increasing the surface area exposed to the passing airflow and/or directing airflow into/over the housing 20.

One or more cooling fan 40 can be provided within either or both of the main enclosure 20 and RPU 30 so as to promote convection cooling. If necessary, either or both of the main enclosure or RPU 30 could be provided with a liquid cooling system in the event that air cooling is insufficient alone to maintain the internal temperature at a desired level.

Figure 3:
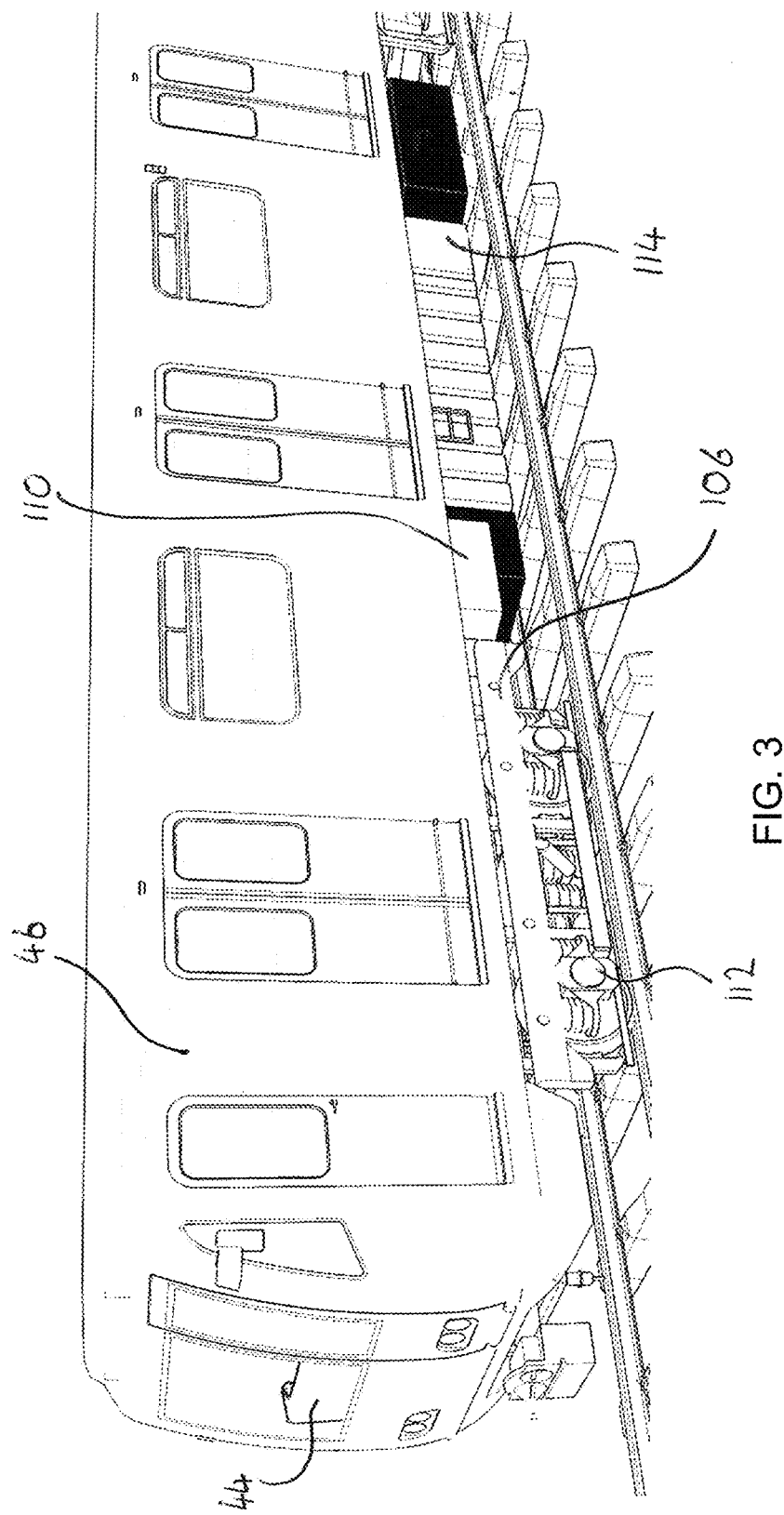
FIG. 3 shows an example of a passenger train to which a system according to an example of the invention can be mounted as an integrated unit.

The main housing further comprises control/management circuitry 42 which monitors trigger/pulse signals, power supply, devices within the TrackVue system 10 and any environmental readings. The management circuitry 42 is responsible for the operational state/health of the equipment and can output control signals to regulate their use so as to ensure equipment operation is maintained within desirable limits. The circuitry is responsible for managing a number of tasks including:

a) Monitoring and regulating internal temperature and humidity of TrackVue with its on-board temperature and humidity sensors. In case these parameters exceed their required threshold, the control circuitry can shut down the power to TrackVue or to individual devices therein. In such an event, an alert will be sent to a display 44 as shown in FIG. 3 of a monitoring console within train 46 and/or to any other relevant communication/monitoring equipment through a Train Information Management System.

b) Monitoring the levels of battery charge and for charging it. This applies to the main battery 28 and/or a battery 48 internal to RPU 30. Any alerts of battery faults or insufficient charge may be reported by alerts as described herein.
c) Modifying the incoming voltage power supply to suit the needs of imaging sensors and laser equipment and for redistributing it as needed.
d) Monitoring and modifying/improving the signal quality of the incoming trigger/pulse signal for controlling the rate of visual, thermal and/or laser scan data acquisition.
e) Permitting and inhibiting camera and laser equipment operation such that those devices are only usable once the vehicle is in motion.
f) Providing an end-user with information on the health status of various TrackVue components through the LCD display 50 on the housing 20 itself, the monitoring console display 44 in the train cab (FIG. 3) and/or another remote console. Rather than the track survey data, this operational data concerns the system 10 health and may be used to understand operational issues, plan maintenance, etc.
g) Pulsing LED lights or lasers in order to reduce power consumption or reduce the heat generated by their use.

In various embodiments of the invention, the main housing 20 comprises a location determining device or module 54. This may comprise a standard GPS or Differential GPS device which records the latitude and longitude position of the vehicle, e.g. at a set frequency.

In various embodiments of the invention, the main housing 20 may comprise operational control devices, such as any, any combination, or all of:

A power supply unit 56 to convert an input current (e.g. at 24 VDC) to a supply suitable for the system, e.g. including cameras and lasers, (such as at 12 VDC or 5 VDC);

A heating device 58 to warm up the housing interior to the minimum operational temperature in case the unit temperature drops below this minimal temperature threshold;

A dehumidifier unit 60 that is able to absorb the moisture from the air inside the unit.

The main housing has electrical/data connectors for communication of data signals with the railroad vehicle and/or powering the TrackVue system 10. A minimum number of external connections may be provided to simplify installation of the system and may comprise a single power connector for the system 10 as a whole and a single external data connector port. However a practical implementation of the system could comprise any, any combination, or all of:

one or more connectors 62, such as internal and/or blind-mate connectors, which allow for the RPU 30 to be mated with the main housing 20. The connectors 62 allow for transfer of data and power.

an external data connector 64 for supply of trigger signal from a vehicle wheel encoder or other suitable vehicle speed input signal;

an external power connector 66 for the taking power from the main power supply coming from the vehicle at an appropriate voltage accepted by TrackVue;

an optional connector 68 for location data or other data input from an external device, e.g. RFID scanner or a third party location detection system aboard the train;

a connector 70 for high speed data transfer through a wired connection, e.g. to the train data bus. This can be used where high volume real-time data needs to be transferred to an external storage on-board the vehicle. This may be required by the end-user to either carry out a more detailed, off-line data analysis, or to review all images collected from the track.

In its current format, the system allows for the use of battery power for short surveys because of limited capacity, and uses power from the vehicle or mains power to charge it. As battery technology continues to develop, it is expected that longer surveys can be carried with battery power in the future. The current design allows for the battery 28 to be swapped easily from its own compartment in the field and replaced with a charged one to carry out recording. The battery charging and capacity status can be displayed on the LCD display 50 and also relayed to the operator console 44 (FIG. 3).

The scan data processing equipment 72-78, associated software modules 79 and data storage 80 are housed within a separate RPU 30 housing. RPU 30 contains all computational equipment for data capture and processing. The RPU 30 comprises a self-contained unit which can process image data independently, provided it is supplied with the relevant incoming image data stream. For this reason, the RPU is provided within its own dedicated housing that is removable/replaceable as a module from the main housing 20.

The RPU 30 in this example comprises computer motherboard 72, high speed processor 74, Field Programmable Gate Array (FPGA) or frame grabber 76, graphics card 78, and a non-volatile data store 80, e.g. comprising one or more data disks, on which are provided one or more software module for processing captured visual, thermal and/or laser sensor data. Thus whilst the software modules 79 are shown as a separate entity in FIG. 1, those relevant processor instructions may be stored, e.g. as executable code, on any suitable memory device within the system. The data store 80 also typically stores the track scan sensor data itself, location data and/or any processed track inspection (i.e. asset classification, defect and/or status) data.

An internal battery 48 for the RPU 30 is provided to ensure that, as a minimum, the internal processing components can be gracefully shut down if the unit is disconnected from the main housing battery or external power supply. Ideally the internal battery 48 would also allow continued data processing, i.e. for image processing jobs already commenced, even if disconnected from external power. The internal battery may also power a communications module for transmission of any relevant messages/data prior to shut down. The battery may power the entire system for a period of time. As battery technology improves, inspections may be performed entirely under battery power.

The RPU 30 has its own communication module 82, typically comprising and a conventional wired or wireless transceiver. The module may allow communications to the vehicle operator in an attended mode of operation, or otherwise to an Operational Command Centre (OCC) in unattended mode. Such a communications module could additionally or alternatively provided in the main housing 20 outside of the RPU. In both cases, the data related to analysis or alerts can also be sent by this unit to the Train Information Management System (TIMS). In addition, a 3G/4G wireless data connection device 84 in the main housing 20 allows external access to TrackVue. The wireless connection can also be used for remote access to perform diagnostics, software updates, and repairs of the unit.

The communication module 82 may serve as an alert transmission unit for sending any alerts due to an adverse track or equipment status detected by either the control circuitry 42 or by the processing equipment within the RPU 30, to a remote location either using wireless or wired connection. The alert may relate to the condition of the system 10 itself, or the track being surveyed.

To allow self-sufficient operation, the RPU 30 may also comprise any of a fan 40 for cooling the unit, a heater 58 and/or dehumidification device 60 for absorbing unwanted moisture in the internal compartment.

The RPU uses blindmate connectors 62 to attach to the main housing 20 of TrackVue body. This allows the RPU to be detached from the TrackVue as required by the operator and can be taken to a back an office environment for data processing as will be described below. The RPU itself forms a completely sealed assembly for outdoor use. The RPU may have a handle (not shown) to aid removal. Status information related to RPU 30 or messages from control circuitry can be displayed directly on a touch panel display 50 which is visible to a human operator when inspecting the system.

Figure 2:
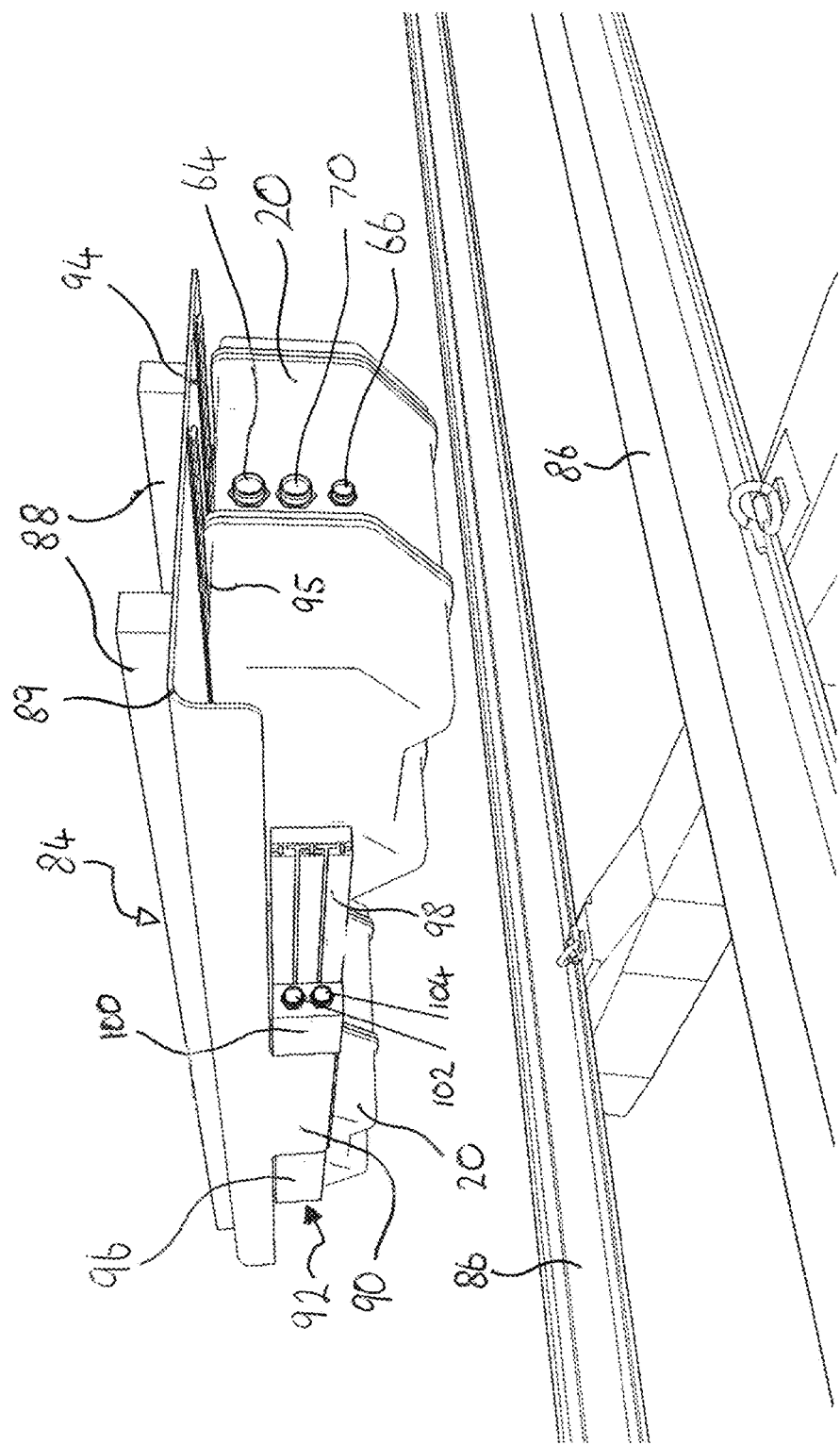
FIG. 2 shows a three-dimensional view of a mounting system for mounting a rail track inspection system to a train according to an example of the invention.

FIG. 2 shows an example of a mounting system for TrackVue 10 in which a pair of housing enclosures 20 are mounted to a common support structure 84. The support structure 84 of FIG. 2 may be used instead of the fixed mount 32 described above in relation to FIG. 1. The support structure 84 extends laterally relative to the rails 86 in use such that the relevant sensors can be held in relation to each rail. The support structure 84 comprises mounting members 88, e.g. so as to define a mounting frame structure for the system 10 as a whole, which attaches to a vehicle in use. Multiple mounting points may be defined on the frame and/or members 88 which can be attached to corresponding mounting points on the vehicle (not shown) using conventional fasteners, such as bolts.

The members 88 take the form of elongate beams so as to provide strength to the mounting structure and also a common support to ensure the correct spacing between the scanning sensors for each rail 86. In this example the mount comprises a panel member 89 having a frontal lip or wall section 90 in front of housing(s) 20.

FIG. 2 also shows the data connectors 64, 70 and power connector 66 discussed above for operation of the TrackVue system 10.

The field of view of a scanning sensor contained within the housing 20 depends on the position of mounting of the housing 20 on the vehicle, the position and orientation of the sensor within the housing 20, and the properties of its lens.

As the vehicle moves, the field of view of the sensor with reference to a fixed position on the track, such as the position of the rail, can change because of track curvature and lateral movement of the vehicle on the rails. The amount of change to the field of view of a sensor depends also on its distance from the vehicle wheel set. If the track curvature does not cause for the rail components of interest to significantly go out of the field of view, the scan data analysis software 79 (FIG. 1) will be capable of their accurate detection and measurement. However for much higher track curvature, the sensor field of view could lose sight of assets of interest. One option to mitigate this would be mount the/each housing 20 as close to a vehicle wheel as possible, e.g. either on the bogie or close to it. In cases where this is not possible, and high track curvature is an issue, it would be advantageous to provide a system for altering the field of view of the sensors. In this regard, each sensor could be individually actuable to keep the relevant track components within the field of view, e.g. by actuation of a lens or viewing aperture to widen/narrow the field of view or else using electro-mechanical actuators to adjust the orientation of the scanning sensors. Additionally or alternatively, the sensors' field of view could be adjusted collectively as discussed below.

In this example, the mounting system 84 comprises an actuation unit 92 for the TrackVue system 10 as a whole. The actuation unit 92 is referred to herein as the 'TrackGlide' unit as shown in FIG. 2. The mounting system 84 comprises one or more runner 94, via which the housing 20 is supported, e.g. suspended, in use. The housing 20 may comprise a bearing structure 95 for mounting on each runner 94 to allow low-friction movement along the runner. The runners 94 extend laterally relative to the track 86, e.g. being aligned with mounting members 88 and allow the housing 20 to be actuated in a constrained, linear manner as a moving platform so as to remain correctly positioned relative to the rails 86.

The actuation unit 92 comprises one or more linear actuators 96 that attach to support 98, which may comprise a linear support. Controlled actuation is achieved using a suitable electrically-powered drive, such as a stepper motor, by way of an encoder 100. The actuation unit has an electrical connector 102 for powering the unit and a data connector 104 for receiving operation commands from an external source such as the TrackVue system 10, e.g. to control the distance and direction of movement of the overall TrackGlide unit 92.

In use, the electrical signal to control movement is generated by the control unit 42 (FIG. 1) under the direction of software 56 which uses one or more scanning sensor (e.g. a laser sensor input and/or a digital image input) to decide on the position of a key reference feature/point on track, such as an edge of the rail. The control unit 42 uses the location of the reference feature to estimate the lateral movement of the vehicle relative to the track that must be compensated by moving the TrackGlide unit 92 (FIG. 2) in the opposite direction.

The TrackVue housing 20 can thus be moved using the TrackGlide unit 92 in real-time, laterally, perpendicular to the direction of the running rail 86, e.g. by the same magnitude as any detected lateral vehicle motion but in opposite direction. This ensures that the TrackVue scanning sensors are at all times in the same relative position to the track as required to keep substantially the same relative field of view of the track. In other examples, the mounting structure 84 including the mounting members 88 and/or panel 89 could be used but without the TrackGlide unit 92 so as to define a static support structure.

It has been found that adjustments to the height of the system 10 relative to the track can be used to implement different inspection modes, e.g. wherein the system can be lowered to provide close rail inspection or raised to provide a wider view of the overall track and its other components. Raising/lowering of the sensors is preferably performed for the system as a whole by providing a suitable vertical actuation mechanism within the mounting system 84.

FIG. 3 shows an example of a passenger train 46, to which the TrackVue system 10 may be mounted using any of the mounting options described herein. The TrackVue system 10 is typically mounted on the underside of the rolling stock, for example on or adjacent a bogie 106 or between spaced bogies 106 of the rolling stock.

The power delivered by the vehicle to TrackVue in its native state may not be 24 VDC and therefore a power converter 110 (typically a DC to DC power converter) as shown in FIG. 3 can be placed anywhere on the vehicle within a reasonable distance of the system, if required, and should provide uninterrupted power at 24 VDC or a desired voltage level via power connector 66 (FIG. 1).

The output of vehicle speed sensor on board the train 46 is used by the TrackVue system 10 in a manner to be described below. In this example a vehicle wheel tachometer 112 is used to correlate travel speed by the rate of vehicle wheel rotation, although a laser Doppler velocimetry device could equally be used. The signal output is preferably a pulse signal provided at a pulse frequency according to the speed of revolution of the vehicle wheel. Typically multiple pulses are provided per wheel revolution. Other suitable vehicle speed indicators could be used provided they provide precise and substantially instantaneous output at a resolution suitable for use as a trigger signal for the track scanning sensors.

The vehicle 46 may comprise a location determination system, which may communicate a current location with the TrackVue system 10, e.g. in addition to or instead of the location determining system within housing 20. The vehicle location determination system could comprise a conventional two-dimensional location system, e.g. a GPS system or the like for determining latitude and longitude. In other examples, the location determination system could determine location as a measure of distance along the track from one or more known track locations. The location determination system could comprise a vehicle travel distance sensor, such as the tachometer 112, and/or a track position sensor. This may be used in addition to, or instead of, a GPS location system. Combining multiple location determination systems/sensor types may be used to increase the accuracy of asset location determination.

The use of a system for determining the distance of travel from a fixed, datum point on the track (i.e. a track position sensor) may be beneficial in pinpointing the location of surveyed track features. A track position sensor may comprise a sensor for identifying track features indicative of known/predetermined track locations, e.g. fixed datum locations. A scanning sensor 12, 24 (FIG. 1) of the kind described above could be used for this purpose or else a near-field wireless communication transmitter/receiver 114 could be employed as shown in FIG. 3. An RFID scanner mounted on the train or as part of the commonly mounted system 10 could be used to detect RFID tags mounted on the track at known locations. A lookup table of known tag locations may be used to determine asset and/or image sensor location.

The operation of the TrackVue system in performing a track survey is described below. The sealed nature of the housing 20 and the dedicated light sources 22 (FIG. 1) allow the TrackVue system to be used for rail inspection at any time of day/night and in varying weather conditions.

The RPU 30 allows two forms of data processing. Firstly, real-time data analysis which uses a combination of either high speed processor 74 coupled with FPGA 76 and/or graphics card 78 to process image/pixel data and/or numerical/point data generated by the laser imaging device. In such analysis, logged imaging results are instant and there is no growing queue of data to process in a buffer. The FPGA and processor are selected to handle the expected volume and speed of incoming data (e.g. without requiring use of a buffer). Secondly, near real-time data analysis is possible using a library of software for high speed processor 74 and/or graphics card 78. Under these circumstances, the analysis is quick but may not be real-time and a buffer of unprocessed sensor data may build up over time depending on the type of analysis being undertaken. Near real-time analysis can be continued after all data acquisition has finished by either keeping the RPU 30 attached to the main TrackVue body 20 on the vehicle 46, or by detaching it and later attaching it to its docking station at a separate location, e.g. back office, as will be described below. Additionally, the data connections of the RPU 30 or housing 20 could be used to offload logged image data in a format suitable for subsequent processing.

The linescan sensor captures a line on the track at a desired resolution and the TrackVue system builds up an image of the track or a section thereof by concatenating the lines together. The imaging resolution in pixel per millimeter in the direction of travel is a pre-set value, for example 0.5 mm per pixel, which may be user specified/altered as required. For an imaging sensor to achieve this, it must be fast enough to accommodate the relevant train speed. The imaging resolution in the direction perpendicular to the direction of travel is based on the lens field of view. For example, if an image width is 1000 mm and 2048 pixels represent it, it equates to 0.48 pixels/mm.

The entire track image data can be constructed as a single image from the linescan output. However it is typical to divide the aggregated image data into smaller images, e.g. with the size of each division being decided based on a predetermined number of line scans, distance covered and/or image file size. In this example, a line scan count is maintained and a single image is defined every 2048 or 4096 line scans. The width of the image in pixels is determined by the imaging sensor capability and may be in excess of 1000 pixels, such as typically 2048 pixels or 4096 pixels, although different resolutions may be used for different requirements.

For any, any combination or all of the above sensor types, the frequency of image (line, area or volume) capture may be controlled so as to be constant with respect to the distance travelled along the railroad. Thus the frequency or resolution over a length of track may be fixed. In order to achieve this, the frequency of image capture or scanning is controlled based on the vehicle speed. In the present examples, this is achieved by use of the vehicle wheel tachometer 112, as shown in FIG. 3, to provide a data capture regulation input, although in other examples a similar control scheme could be implemented using any other conventional vehicle speed sensor or odometer.

For a predetermined distance of travel, e.g. as sensed by a predetermined number or fraction of wheel revolution on the tachometer, a pulse signal is output to the relevant image capture device to initiate an instance of image capture, e.g. as a frame/area, line or region scan. Therefore, if the train accelerates, the relevant sensor(s) will scan more quickly, and if the train decelerates, the scanning rate is lowered accordingly. The operation of multiple imaging sensors, including digital cameras and/or laser sensors, can be synchronised such that they each trigger their data sampling at the same time. The raw data for different sensors at a common time/location can thus be cross-referenced within the indexed data store record.

The wheel tachometer 112 (FIG. 3) provides a fixed number of pulse signals to the TrackVue connector/interface 64 (FIG. 1) for every wheel rotation thereby providing data on overall distance travelled, and speed of wheel rotation. The number of pulse signals is specified in terms of a fixed value per rotation. The wheel tachometer 112 pulse output rate is selected to work for a given maximum vehicle speed at a desired level of image resolution, e.g. such that the maximum scan rate is within the upper limit of the scanning sensors 12. TrackVue architecture is independent of the choice of the tachometer or speed sensor and can receive any suitable pulsed or other frequency control signal at interface 64. For example, both wheel tachos fixed to the wheel or portable versions using laser Doppler can work as they provide a trigger in a suitable format, such as transistor-transistor logic or low voltage differential signaling format.

Figure 5:
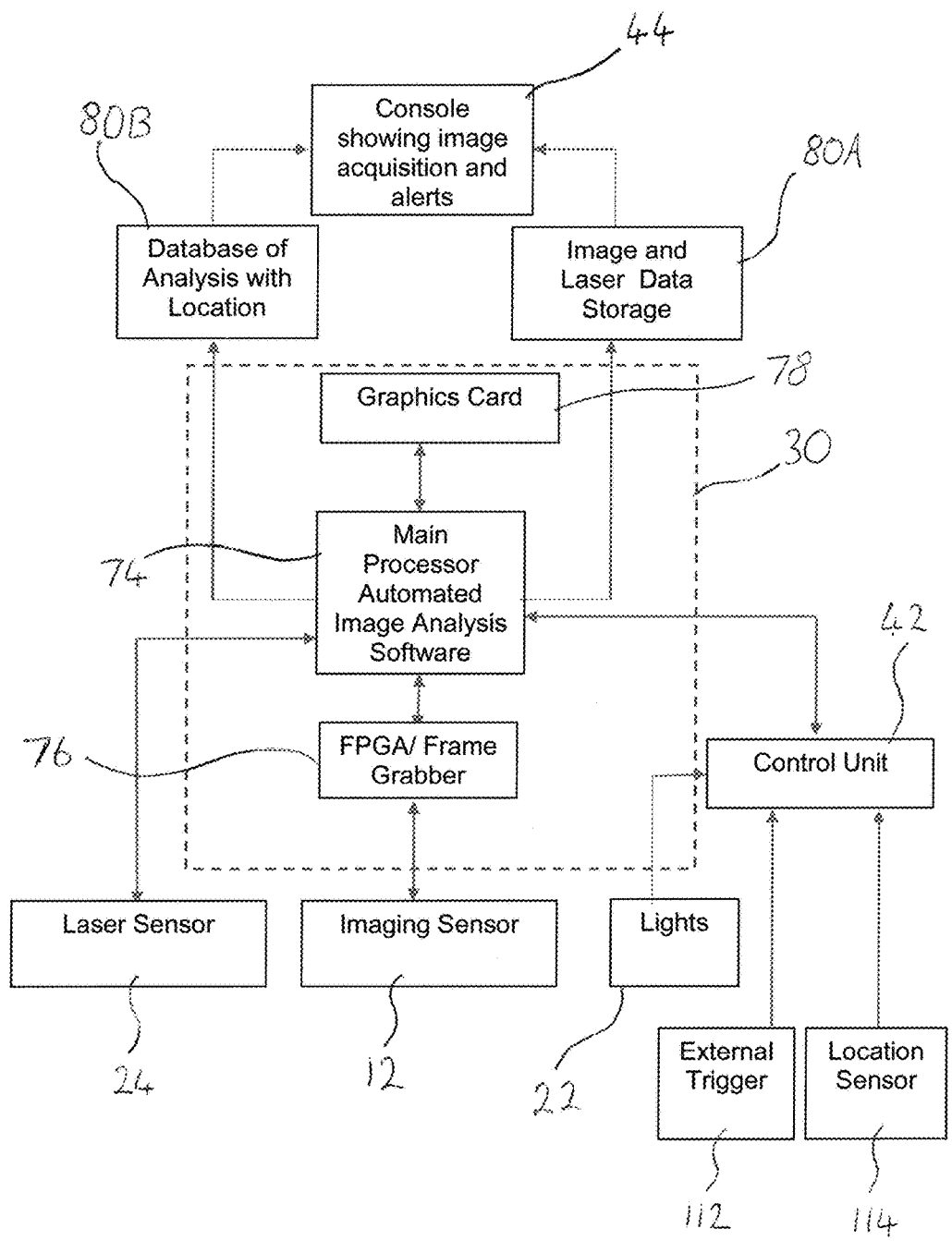
FIG. 5 shows a schematic arrangement of data flows between different components of a system according to an example of the invention in use.

FIG. 5 details the overall data flow process (including the flow of control signals and track inspection data outputs) from sensor 12, 24 outputs to the alerts/reporting tools for the end-user being displayed on an end user device 44 (FIG. 3), including the scan/image data processing stages to analyse track components. Like reference numerals are used to depict like features described above in relation to FIGS. 1-3. Any, any combination, or all of the process stages may be automated in accordance with examples of the invention. The use of modular software 79 (FIG. 1) and/or hardware 72-78 allows the data processing to be segmented into a plurality of tasks or 'levels', having the benefit that one or more level can be prioritised or handled separately from one or more further level.

The image 12 and/or laser 24 sensors record data which is passed on to the main scan data processor 74 on-board TrackVue, comprising one or more high speed processor. The sensor data output may connect directly to the main processor 74 if no image compression is desired. If real-time compression is desired, e.g. to JPEG format, the data flows from imaging sensors to one or more FPGA or image grabbers, 76 which compress and reduce the quantity of data whist retaining the maximum possible image quality for further examination. The FPGA 76 also serves as the hardware used for real-time scan data analysis and would work together with the main processor 74 to load appropriate image analysis software 79 for analysing scan data. The number of input connections on an FPGA 76 may be limited and therefore if several imaging sensors need to be connected then more than one FPGA board may be employed.

The main image processor 74 can also use an array of graphics cards 78 to process image data using real-time or near real-time data analysis, or simply store it in memory for analysis at a later time. The raw data is passed from the sensors to system memory for storage in parallel to sending it for processing. The use of graphics cards allow the main processor to spread the load of image analysis on multiple parallel cores significantly reducing the time to process image data. The data for laser image acquisition is handled in exactly the same manner as image data unless the laser device 24 (FIG. 1) has an internal data processing capability, in which case data from it is directly passed to the main processor 74 bypassing FPGA 76 and/or graphics card 78.

The overall system of processing uses multiple software modules. The main processor 74 decides which software algorithm must be used for which sensor data from a pool of algorithms available within the data store. The implementation of the software algorithms is different for different hardware, for example, whether they need to be executed on a graphics card or FPGA. A software module or routine is a self-contained software tool which can take an image frame (typically in data format as a matrix of numbers) or laser data (as a one, two or three dimensional matrix of numbers), and apply a series of arithmetic operations to process either the contents the incoming data represents, or to make measurements within such data.

A first software tool is for image and laser sensor data acquisition and controls the process of acquiring data including data flow from sensors, compression, sending it for analysis, recording it with a location (and optionally a timestamp) and storage on the physical hard disk 80 as a scan database 80B.

All raw data needs to be stored to a physical memory 80A in addition to presenting it for analysis to appropriate processing hardware. For high speed data acquisition, storing JPEG images in real-time may be time consuming and therefore pixel data will be stored in a flat file structure which can be converted later into JPEG data by adding header information to it. Laser scan data in compressed format are also stored in the non-volatile data store 80. The location for storage in terms of data directory can be specified by the system operator. The system maintains a database record 80B in the data store 80 that stores for each raw data image collected, its location including GPS latitude and longitude coordinates and/or a railroad line reference position. In cases where RFID location data is available, this will be stored in addition to, or instead of, other location data.

A second software tool is for image and laser sensor data analysis and is responsible for executing a number of processing routines/algorithms on the collected data in either real or near real-time. If on-board data analysis option is not chosen, no data analysis is performed while data is collected. All data analysis in such cases is performed offline in a back office environment. For such cases, an FPGA can be replaced with a simpler frame grabber board which can only acquire data but cannot process it.

As the first stage of data analysis identifies the contents of interest within an image, e.g. identifying one or more data features that may be indicative of its contents. In case of two dimensional images, a matrix of numbers representing an image record for each position/pixel within the image, either a single value denoting the brightness of that pixel, or three numbers representing the red, green and blue channel color values for that pixel.

One or more arithmetic operation is used to cluster pixels of similar properties that are adjacent to each other, e.g. according to an image segmentation process. The image is thus broken down into a series of clusters by assigning pixels to clusters according to brightness/colour and proximity to other pixels of the same/similar properties. For each identified cluster, a series of further operations are applied that determine one or more property for the cluster, thereby defining a feature of the cluster that may be indicative of a corresponding feature of an asset captured in the image. The cluster properties assessed at this stage may comprise any or any combination of a cluster edge, colour, texture, shape, pixel intensity and/or one or more other statistical property.

A general assumption is made that all pixels clustered together represent the same object/component given their visual similarity. The process keeps track of which pixels (intensity value and coordinate positions within the image) belong to which cluster. A pixel can only belong to one cluster at a given time.

The identified properties of each cluster can be used by a classifier (e.g. a software tool that classifies or recognises the identity of objects in image data based on what it has been trained to recognise). Thus classification of each pixel cluster is used to classify the track components represented by the clusters. Feature analysis and track component classification can be performed by separate modules.

In the analysis process, a range of artificial intelligence algorithms that build upon statistics and machine learning principles, coupled with semantic knowledge of track layout that defines the probability of assets in different parts of the image, are used. The integration of semantic knowledge or domain knowledge about track layout helps software automatically eliminate false detections in analysis, and provides a better recognition rate on objects of interest (track components or defects).

The classification process/module matches the properties of each cluster to those of known objects (e.g. rail or sleeper). This process is known as feature based matching. In some cases, an image template of the known object may be matched or correlated against the cluster of pixels directly. This process is known as template matching. With either form of matching (feature or template based), if the level of match is greater than a pre-set threshold, the cluster is labelled to be the same as the object matched.

Unmatched clusters are assigned to be a part of the background.

The number of properties/features matched depends on the complexity of known objects, and has a direct bearing on the complexity of the analysis algorithms and time taken to match. Once a scanned track component/object is labelled, the system stores a database record 80B in the data store 80 comprising any, or any combination of: the image sequence number where the object was found; a time stamp and/or location record of where the object was imaged on the track; an object label; object properties within the image (e.g. any or any combination of information on its centroid coordinates within the image, dimensions horizontal and vertical, coordinates of points of interest or boundary pixels, colour, edge and/or texture and/or shape data), position of the object relative to track centreline or running rail (field side or gauge side).

Based on the degree of match achieved with a known track component, the system allows logging of a confidence score or rating in the relevant database in the data store 80, e.g. at 80B. A numerical assessment of the similarity between the imaged component and the predetermined component features or template feeds into a confidence score represented as a value on a defined scale, e.g. between 0 and 100, whereby 0 represents no confidence and 100 represents highest possible confidence. The confidence estimate is directly based on the level of match determined between the properties of a pixel cluster in the image, and of those of known objects, and takes into account the visibility of the object (e.g. excess ballast estimates around recognised objects provide a measure of visibility of objects).

The image analysis process follows a hierarchical approach. First, key reference assets are recognised (see FIGS. 6 and 7) including rail top 201, rail side 202, rail foot 203, ballast 204, sleeper 205, slab track 206, plates 232, switch 217 and third/electrified rail 41.

A second stage processes pixel data from a smaller image area of interest comprising the image area covered by reference objects identified in the first stage and their surrounds. This is aimed at further identifying smaller objects of interest (e.g. spikes, or fasteners) which are then labelled as before.

In the third stage each reference object and the further objects are thereafter analysed for defects. The condition/defect analysis may comprise one or a plurality of dedicated software modules. In general, the tool will compare the amassed image data for the identified object against a predetermined (i.e. a nominal or previously recorded) object model. The precise details of the model and/or the comparison undertaken will typically differ between different track component types. In certain respects this may be similar to the feature/template matching process described above, except that now that the component type is known, the differences between the imaged object and the predetermined model can be extracted and/or quantified to provide an account of the track component status.

A comparison may be made between geometric attributes of the predetermined and scanned components, for example such as the component orientation, e.g. angular orientation or relative position, or one or more component dimension. Comparison may be made additionally or alternatively between surface properties (texture, colour) of the predetermined and measured components, e.g. including continuity/discontinuity of the surface.

The geometric and/or surface condition of an object can be analysed for detecting: (a) Wear and tear of the component; (b) Broken components; (c) Change in orientation of a component or part thereof, indicating damage; (d) Missing components if prior information is available on what components are expected on a given portion of track; and (e) Components obstructed from view because of snow, mud, leaves or sand thereon. Imaging sensors can evaluate component condition based on its visual appearance, change in colour, presence of edges which can represent cracks, change in object boundary orientation and so on.

At a basic level, the system can report on the presence or absence of a component defect. Once detected, it is also possible to determine further characteristics for known of identifiable defect types, such as: defect classification (type of defect, name); defect severity (a grade value); defect properties (size, shape, colour, orientation and so on); and/or defect change (measurements showing change in properties over time). A simple example may be a crack, the length and width of which may be tracked over repeated scans as the crack propagates over time. Similar techniques may apply to the dislodging or warping of components over time but may equally apply to instantaneous defects that can be compared to previous scan results or known defect types.

Figure 6:
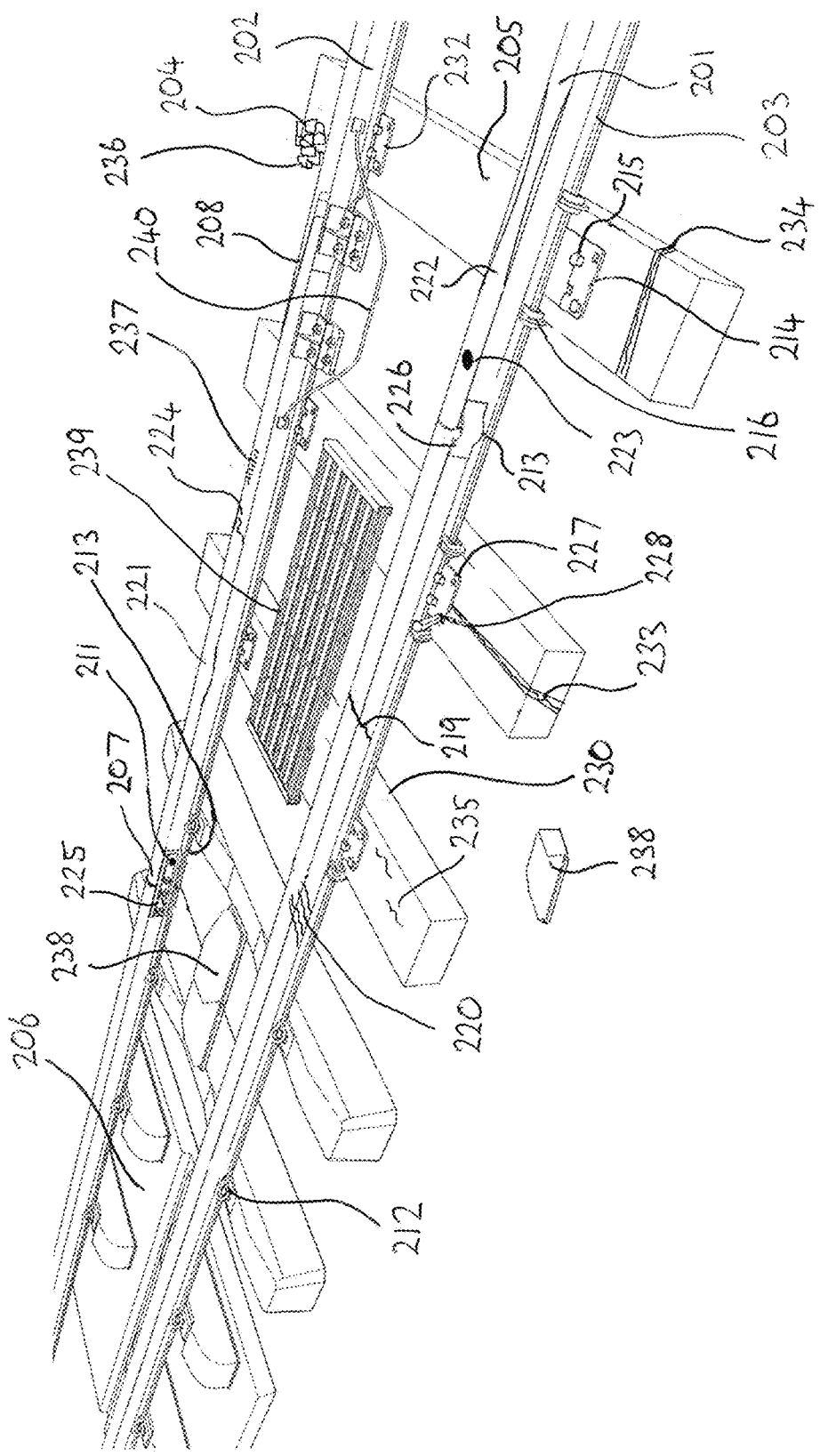
FIG. 6 shows a three-dimensional view of a section of rail track, including examples of track features that may be inspected by use of the invention.
Figure 7:
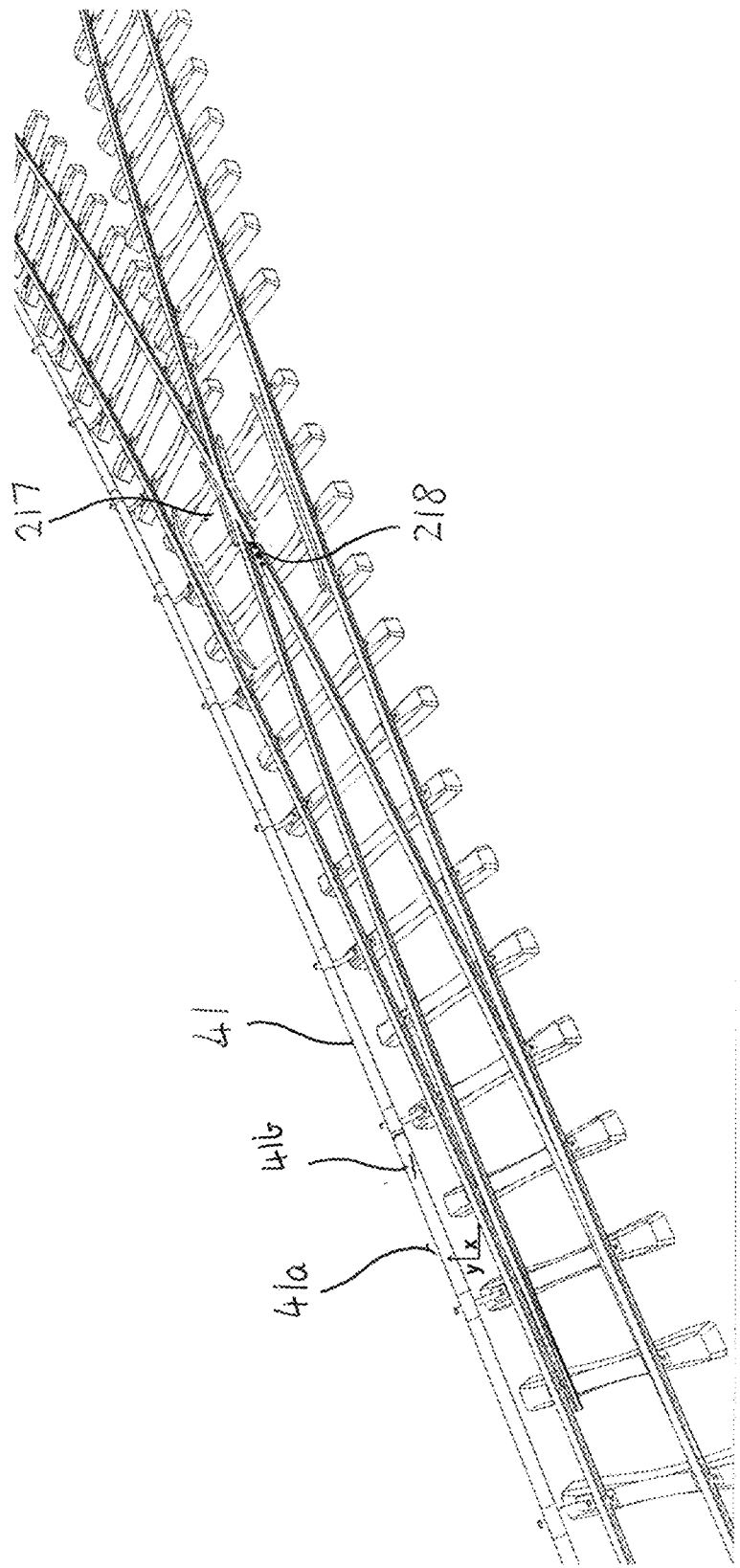
FIG. 7 shows a three-dimensional view of a section of rail track including a junction or switch which may be inspected in examples of use of the invention.
Figure 8:
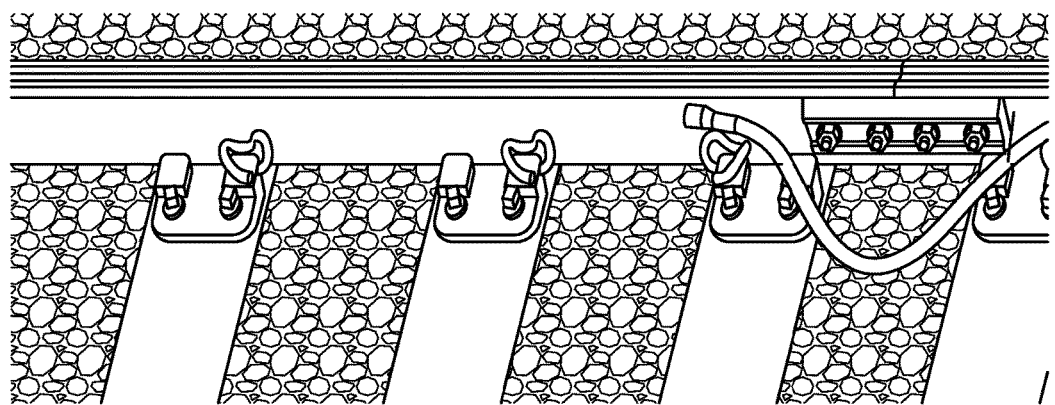
FIG. 8 shows an example of a digital image taken by a system according to the invention of a rail side and surrounding track.
Figure 9:
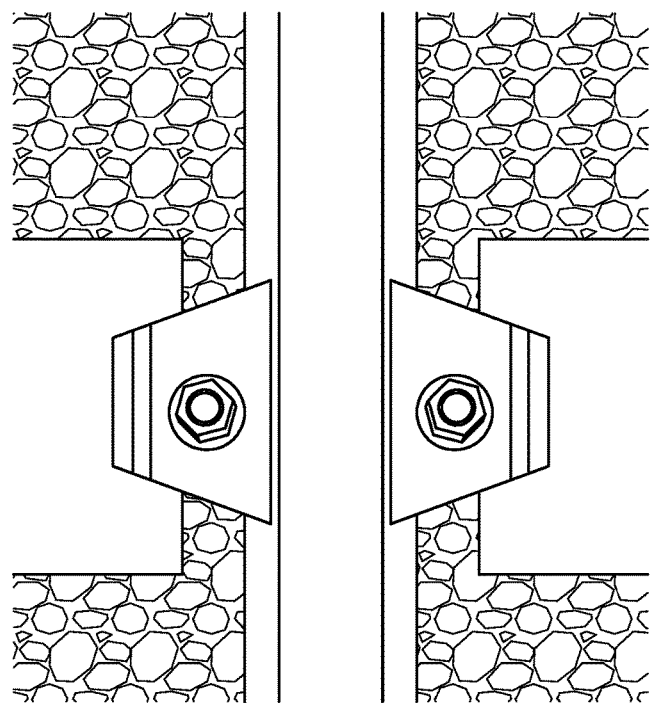
FIG. 9 shows an example of a digital image taken from above by a system according to the invention of a rail head, fastener and plate area.

With reference to FIGS. 6 and 7, identifiable defects can be either caused by poor rail wheel interaction (rail wear 221, squats and wheelburns 223, switch defects 218, running band deviation 222), excessive stress on track components causing fracture or components to break away (gauge corner cracking 220, cracks on rail 224, cracks on fishplate 225, breaks 233 and cracks 235 on sleepers 205, abnormal rail joint gaps 207, missing bolts on fishplates 211, missing fasteners 212, rail discontinuity/break 219, missing spikes 227, raised spikes 228, missing anchors 230, base plate 232 movement either laterally or vertically, defects on electrified rail 41b), temperature variations (abnormal expansion join gaps 208), and movement of the position of running rail or electrified rail 41 (electrified rail position with reference to running rail measurements 41a). The defect sizes and severity data is stored in memory 80. The memory 80 also stores information on rail track assets (image objects) and defects (abnormalities within image objects) within a suitable cross-referencing database structure. For example, as shown in FIG. 5 separate entries are made for the analytical results at 80B and the sensor data storage itself at 80A. This can be achieved using separate tables within a common database or separate, cross-referenced databases to store location of image data on disk, identified assets and defects with their properties, and time and location information.

A set of domain specific rules may applied on defect recognitions to rule out false positives. This can be applied as a post-process on the database table of defects 80B, or the scan analysis software 79 can apply this knowledge when identifying assets as part of the process described above.

Where digital imaging sensors are used, the identity of certain track components or defects can be confirmed through their identification with laser scan analysis of the track bed. Laser scan data analysis may also be used independently to identify track components, features and/or defects, e.g. for components that are not readily perceivable using digital images or when a digital camera is unavailable. Laser scans provide valuable depth information which can represent certain defects on components. A sudden change in depth profile of one component may be normal for some, and abnormal in other cases. For example, a change in depth profile of ballast/sleepers may be fairly normal, whereas, one does not expect the same on a railhead where it should be flagged as a defect.

First, locations/points of curvature change in laser scanned surface profiles are measured which denote the edges of objects. The distance between two successive high curvature points is measured and evaluated for identity using a set of rules. For example, a raised segment with length close to 80 mm represents the railhead provided another such segment can be identified at further a distance equal to the gauge of the track. Thus in different aspects of the invention, whether using laser or camera imaging, proximity/distance between assets or track features can be used to classify the track components as being of a predetermined type.

Laser and image analysis processes share several common components. Each system's sampling rate can be controlled by vehicle speed using data from a shared wheel encoder 112 (FIG. 3). The control unit 42 (FIG. 1) ensures that the correct trigger and appropriate power is delivered to both imaging and laser components for operation. These systems also receive time and location information provided by the same external time sensors and location sensors. The level of sharing of data acquisition and processing devices such as FPGA, graphics cards, processor, disk memory and others depends on a chosen design and construction of the TrackVue system 10.

The modular architecture of software for image and laser data acquisition and analysis provides possibilities of further interaction. In one scenario, it is possible for linescan and laser data analysis to be completely independent. In another scenario, linescan data analysis information can be used to trigger a laser measurement or vice-versa. For example, the detection of plates 214 (FIG. 6) in linescan imagery can trigger laser based measurement of plate 232 movement (e.g. laterally and/or vertically). In another use scenario, laser and linescan measurements can be correlated so that one set of measurements confirms or discredits the presence of an object (e.g. a fastener 212 or plate 214 in FIG. 6). Additionally or alternatively, the laser and linescan analysis can be cross referenced to provide additional context/meaning to laser measurements. Linescan analysis can provide details of object identity that lies under a projected laser beam such that measurements can be labelled and make sense.

One or more laser data processing software module forms a part of the overall image analysis software 79 (FIG. 1) and is responsible for object recognition and measurement. TrackVue 10 uses laser technology to make a number of such detections by evaluating the size, orientation and curvature of a laser beam pattern (line, spots or grid) within a 2D grayscale image. With reference to examples in FIG. 6, this technique can be used to determine (a) rail wear 221 on rail top 201 and rail side 202; (b) missing bolts on fishplates 211; (c) missing fasteners 212; (d) welds on rail foot 213; (e) plate depth movement 232 over the sleeper 205; (f) depth of railhead defects such as tamped joints 207, squats and wheelburns 223; (g) switch defects 218 (FIG. 7); (h) the position of running rail with reference to the position of electrified rail 41a; (i) measure gaps in electrified rail and abnormalities 41b; (j) unacceptable wear of electrified rail 41b.

Using the techniques described above, a significant variety of track components, sub-components and defects can be identified and assessed, including, in addition to the features described above: rail grind marks 237, welds 213, weld clamps 226, excess ballast 236, signaling assets 238, magnets 239, cables 240, wheelcut 234, present or missing fasteners such as spikes 215, and anchors 216. For any track components or sub-components for which a predetermined spacing or orientation is expected relative to one or more further components, the processing steps described herein may be used to determine an amount of skew, misalignment or deformation for the measured component.

Figure 10:
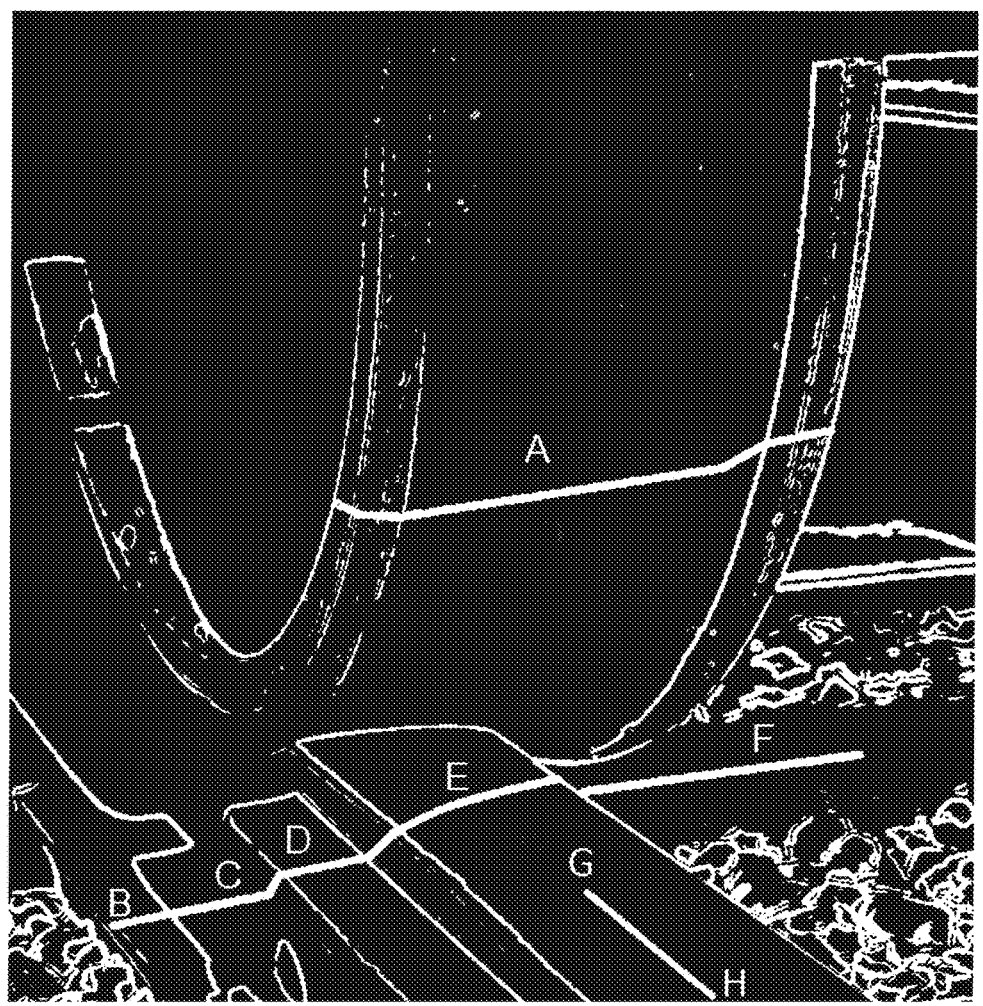
FIG. 10 shows an example of a further type of image, i.e. a laser-derived image, of an interface region between a railroad vehicle wheel and a rail captured by a system according to an example of the invention.

FIG. 10 shows the position of laser line patterns on rail, plate and surrounding areas to make depth measurements as an illustrative example of how the laser beam pattern (a line in this case) can be projected across running rail features/components shown in FIG. 6. The relative differences in orientation of the beam in sections B (over a sleeper 105) and C (over a plate 232) can provide details on vertical plate movement. Changes in beam straightness in section D (over rail foot 103) can provide data on the presence of fasteners 212 and welds 213. The corresponding curvature of beam between sections D (rail foot 103) and E (rail head 101) can provide data on rail wear 221. Beam straightness in section F (sleeper 105) can provide data on whether the beam is on a sleeper 205 (e.g. a smooth surface) or ballasted area 204 (e.g. an irregular surface). The orientation of laser beam projected axially along a rail itself shown as section GH can be used to determine the rail slope and identify defects such as dipped or spaced rail section joints 207.

An optional laser beam A projected onto the railway vehicle wheel can provide further information for the measurement of the distance between the wheel flange and the edge of the rail. This can provide additional or alternative analysis of rail wheel interaction.

The scans generated by the laser unit can be analysed using one or two dimensional data analysis, or by first building a three dimensional surface and then applying three dimensional data analysis algorithms for determining the geometry of components, and further estimating their identity based on dimension and shape measurements from such profiles. The profiles are subject to noise and without information typically associated with imaging sensors such as color and/or brightness/texture, the component recognition software for analysing laser data alone achieves limited success. The asset identification and status assessment algorithms have been found to achieve better accuracy on asset recognition by combining laser sensor data analysis with imaging sensor data analysis wherever possible.

Thermal imaging sensors can also be used to identify and/or detect defects in track-related assets or components. Thermal images may be attained using digital images in the thermal/infra-red or near infra-red band of the electromagnetic spectrum. Taking of thermal images may be triggered in any of the ways described above for visual images and/or laser scans. The processing of thermal images may be less rigorous and may be used simply to identify the presence or absence of a heat source, e.g. as an elevated temperature region above ambient. Additionally or alternatively, thermal images may be processed in a manner akin to visual pixel image data in order to identify pixel clusters and associated features of components. Thermal images may be used independently to assess the presence/status of a component or in conjunction with the camera and/or laser scan data to improve the certainty with which components can be analysed. In one example, the absence of an expected heat signature may be used to indicate a defect, such as a broken cable or connection, which may or may not be identifiable in other scan data sources.

Using the above techniques for component classification, the system may also serve as a novelty/anomaly detector. In the event that foreign bodies are detected using the available sensor data that do not match any predetermined asset models/types (e.g. that do not meet minimum threshold confidence levels), or that were not present in previous surveys, the relevant processor 72-78 and/or software module 79 of FIG. 1 can output a finding of an unclassified object. The visual images and/or laser scan data in which the anomaly is present may be logged and an alert output identifying the presence of an anomaly, e.g. including its location. Manual input may be required to identify the asset type, if necessary to update the record after inspection.

In any of the examples described above, it will be appreciated that the data store 80 may comprise a database of known track component types, e.g. comprising a collection of pertinent component surface/color features, ranges of geometric values, edge features and/or other features such as temperature or surface texture. The captured scan data can thus be compared to any such predetermined features or associated numerical values when identifying components. The collection of predetermined feature values for known components may thus represent a computational model of a component type.

Figure 4:
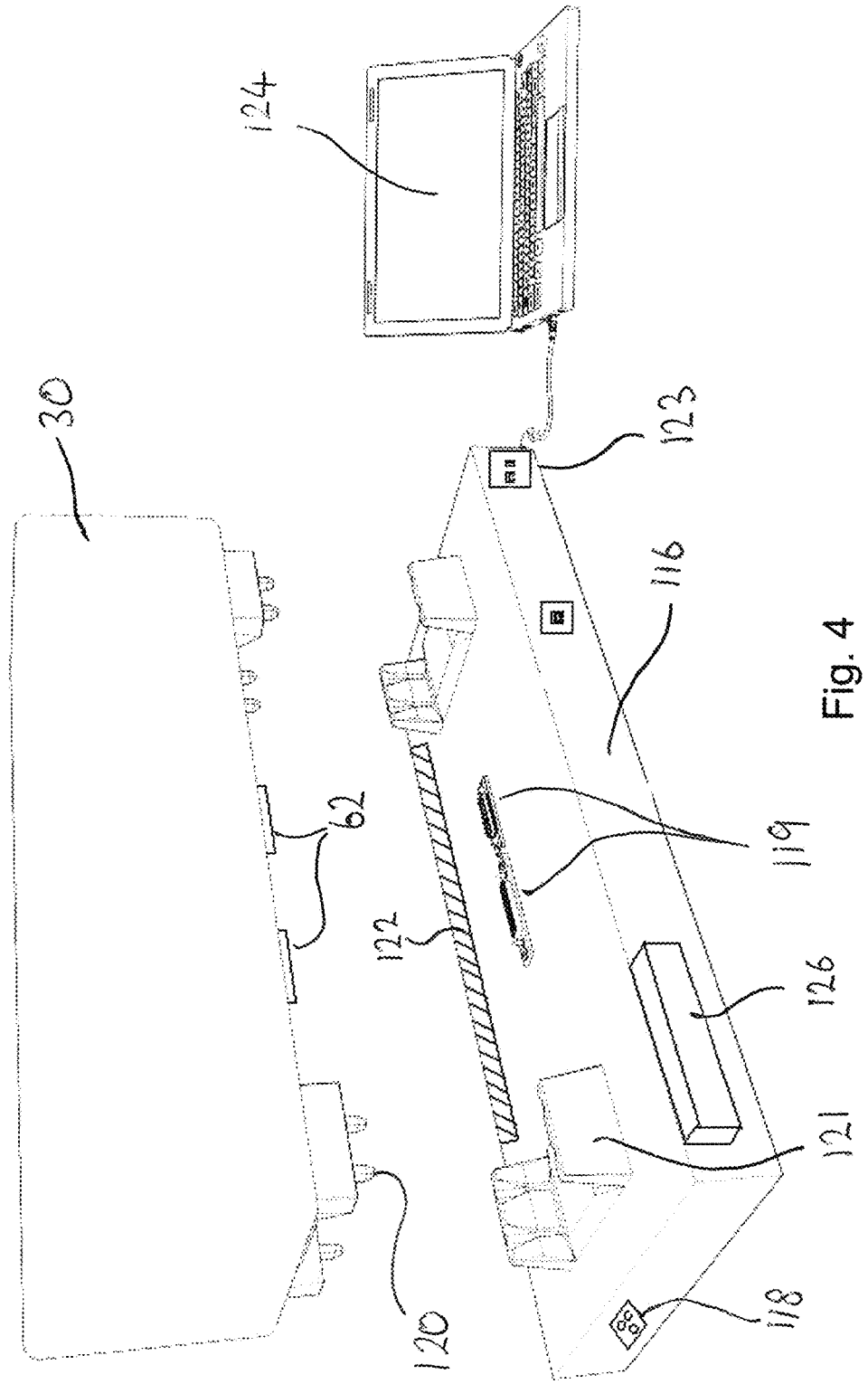
FIG. 4 shows an example of a removable processing unit (RPU) according to an example of a system according to the invention.

Whilst the above system is described in terms of on-board processing steps, the real-time image data logging allows subsequent analysis of the captured data for track asset recognition and status assessment. FIG. 4 shows a user console or system by which imaging data stored by the RPU 30 can be analysed at a later time (offline processing) after data capture. For offline processing, the RPU 30 can be detached and used within a back office environment. It requires a docking station 116 within such an environment to receive power for continuing data analysis operations.

The docking station 116 takes power from a mains supply via a suitable power connector 118 and converts it to power that can be used by the RPU 30 by using a suitable power converter. Correct docking is assisted through the use of guiding pins 120 which align into corresponding docking formations 121 in the station 116 for a secure mechanical and electrical connection. Other electromechanical connectors may be used. The power/data connectors 62 of the RPU 30 are received by corresponding connectors 119 in the docking station 116. In order to keep the RPU and the docking station 116 cool for extended periods of operation involved in any offline data analysis or review, a cooling unit 122 in the docking station 116 using either air/convention, conduction cooling or liquid cooling may be used. In order to use the data within the RPU for review and reporting, or for downloading or uploading files, the docking station can be connected to a computer 124 which can access the RPU through it using a standard data connection, e.g. USB or Ethernet/RJ45 connector 123. The RPU can be connected to a local network for remote access through the relevant network connection. The docking station 116 may also have a power converter 126 to convert a conventional mains AC supply to a DC supply for powering the RPU 30.

In summary of the above description, TrackVue can offer a compact solution whereby all sensor and processing equipment may be packaged inside a singular rugged assembly. The solution is designed for easy attachment to a range of vehicles, especially passenger and inspection trains, and is significantly more compact than conventional track surveying and inspection systems that use separate in-cabin and out-cabin equipment. TrackVue is designed for low power consumption, which is a critical enabler for use on passenger trains, by reducing the number of electrical components used, improving system design, and by selecting low power yet high performance components. The external dependencies for operation of TrackVue are significantly reduced compared to existing inspection train systems and can use wireless communication with an operator console 44 (FIG. 3). The overall design therefore significantly reduces the cabling/installation burden as all connections between the camera and laser equipment, processing equipment and data storage are internal to TrackVue enclosure.

TrackVue can work in both "attended" and "unattended" mode. In the "attended" mode, the operator starts track surveying and inspection process by powering on the system through a console application which allows them to change any settings if needed before the start, otherwise, default settings apply. As track is surveyed, any alerts are fed back to the operator on their console 44 (FIG. 3) through a desktop application which provides real-time display of images and/or statistics on surveyed track. For real-time image and laser data analysis, any assets detected are presented to the operator and can be overlaid on a map or other on-screen visual track representation. In case of near real-time scan data analysis, a pool of image/laser data waiting to be processed is maintained and recorded in database. The position of the vehicle using one or more location sensors (e.g. GPS, line reference, RFID) can be displayed for all tack components and/or data collected. One, two or three-dimensional plans of the surveyed route can be generated using the surveying system described herein, in which the track and relative locations of identified components/defects are marked.

At least one wireless or a wired connection is established between the system enclosure and the console 44 mounted inside the vehicle for operator inspection and/or use. This can transmit in real-time information on raw data, track components, their condition, measurements, and system status to the operator which can be displayed on the console 44.

A reporting tool allows for a range of asset survey reports and graphs to be generated. The format of reports and graphs is optimised for the end-user. Any problems associated with TrackVue performance or malfunction is displayed for correction at the operator console. At the end of vehicle run, the console also displays the current status of data analysis. If real-time analysis is chosen, all analysis is finished at the time of the end of the current run. In case of near real-time analysis, the console shows the amount of data waiting to be processed. At this stage, the operator has the option of continuing on with the analysis, or to stop the analysis. Any unfinished analysis can be carried out the next time TrackVue is started or by removal of the RPU and attachment to a power source, e.g. such as a docking station within a back office environment for completing all remaining data analysis. In this case the RPU serves as a replacement for data analysis in a back office environment. Once the data analysis is complete, the results can be offloaded from it through a USB connection by copying track imagery and results database, or by simply removing a detachable disk.

A separate offline desktop software can be used by end-users in an office environment to perform a number of tasks including: (i) Reviewing of detected tack components and their condition using rail route maps or other GIS maps where available, and applying tools for eliminating any false detections; (ii) Generation of survey reports for maintenance detailing track components and their condition; (iii) Comparison of analysis from multiple previous runs to see the changes in track condition; (iv) Generate a risk assessment report for identified track components; (v) Generate a labelled plan of the track; (vi) Generate a report detailing novel features on track, for example excess sand, mud or snow, or unusual objects; (vii) Print or export to portable devices various defect data, reports and any other statistics; (ix) Plan maintenance for short or long term strategic planning on equipment repairs or replacement; (x) Plan for any track renewals; (xi) Exporting analysis to a centralised Engineering Data Management System which contains a wider set of track condition information; (xii) Exporting analysis to any web-portals or external databases; (xiii) Exporting analysis to portable devices which can be used by track engineers to walk the track; (xiv) Comparison of automated data analysis reports with relevant track maintenance or track walking records to audit their quality; and (xv) Review imaging sensor data analysis integrated with laser scan data. Any of said tasks may be performed by the on-board TrackVue system as necessary in other implementations of the invention.

During use on-board a railroad vehicle, in an "unattended mode", the system starts automatically on receiving power from the external source. Data acquisition sensors and lighting units are triggered to start operation once data from the wheel tacho or other suitable signal input confirms that the vehicle is in motion. If the vehicle stops for a period greater than a pre-set threshold, the sensors stop recording. The system does not require a console to display data acquisition or defect analysis. Instead, the results are transmitted to the Train Information Management System (TIMS) directly, or through email/wireless communication to an external Operation control Centre (OCC). Any further actions taken on such communication is the responsibility of TIMS or CCC. In case if a "near real-time" data analysis approach is employed on an unattended system, it is programmed to continue data processing as long as mains power or battery power is available and buffer data analysis for future runs if needed.

The system can be used for a wide variety of tasks including track component recognition and registration, track condition monitoring, change and degradation detection, track risk evaluation, generating maps of track with assets/defects embedded within such a map, detection of novel and threat objects, and measurement of track/rail properties such as curvature. Thus the invention may allow plotting the analysis results with the available location data to produce Geographical Information System (GIS) maps for print or export. By repeating the analysis at regular time intervals, changes in component conditions and the associated level of risk can be determined.

The system can thus be used to generate risk reports on track sections which will contain information on track defect identity, position, and/or risk severity. Reports containing information obtained through use of the invention may be used for planning track checks, maintenance, repair/renewal, removal and/or replacement.

What is claimed is:

1. A railroad track inspection system comprising:
   a plurality of track scanning sensors;
   a data store for storing track scan data recorded by the track scanning sensors; and
   a scan data processor for automatic analysis of said track scan data upon receipt thereof to detect one or more track components within the scan data from a predetermined list of component types according to one or more features identified in said scan data;
   wherein the system comprises a common support structure to which the track scanning sensors, the data store and scan data processor are attached, the common support structure having a mounting for attachment of the system to a railway vehicle in use; and
   wherein the track scanning sensors are adjustably mounted on the common support relative to the mounting, and the system comprises an actuator and a controller for dynamically adjusting a field of view of the image capture sensors whilst the vehicle is in motion, the actuator being a common actuator arranged for translation of the track scanning sensors in unison relative to the support structure mounting.

2. The system of claim 1, wherein
   the plurality of track scanning sensors comprise one or more visual imaging sensor and one or more track geometry measurement sensor system using three dimensional surface profile measurement;
   wherein the system comprises a motion sensor and the scan data processor receives the output of the motion sensor and the geometry measurement sensor so as to determine a three-dimensional position of track components in space;
   wherein the motion sensor is attached to the common support structure.

3. The system according to claim 2, wherein the common support structure comprises a rigid enclosure within which the track scanning sensors, the data store and scan data processor are housed as a single module or assembly.

4. The system according to claim 3, wherein the scan data processor and data store are provided in a housing as a removable processing unit, which is releasably mechanically and electrically coupled to the common support structure by one or more connector formation.

5. The system according to claim 2, wherein the system is arranged to operate selectively in both an attended mode in which a human operator provides control inputs for image data acquisition, wherein operator software tools are available for review and reporting of asset status information, and an unattended mode, wherein the system operates fully autonomously according to a preprogrammed set of machine readable instructions embedded within it.

6. The system according to claim 5, wherein the unattended mode does not require human intervention for starting, stopping, data acquisition or analysis and is fully automated from data collection to transmission of data analysis to an operational control centre.

7. The system according to claim 4, wherein the scan data processor and data store are provided in a housing as a removable processing unit, which is releasably mechanically and electrically coupled to the common support structure by one or more connector formation.

8. The system according to claim 7, wherein the track scanning sensors are mounted to the common support structure separately from the removable processing unit.

9. The system according to claim 7, wherein the removable processing unit comprises a sealed unit, an internal space of which is isolated from an interior of the rigid enclosure when connected thereto.

10. The system according to claim 9, wherein the track scanning sensors are mounted to the common support structure separately from the removable processing unit.

11. The system according to claim 3, wherein the enclosure comprises a plurality of window portions, each portion being arranged in the field of view of one or more of said track scanning sensors, wherein at least one window portion is arranged at a different angular orientation to at least one further window portion.

12. The system according to claim 3, wherein the common support structure and/or housing comprises a common power supply device and/or data connection device for connecting the system to the railway vehicle.

13. The system according to claim 2, further comprising:
a battery arranged to power at least the scan data processor and/or sensors such that storage and/or analysis of the track scan data can be performed by the system for a period of absence of external power.

14. The system according to claim 1, comprising one or more light sources attached to the common support structure and arranged to illuminate a region of the railroad track corresponding to the field of view of the track scanning sensors.

15. The system according to claim 14, wherein the illumination from the light source is substantially uniform over a lateral section or width dimension of the track.

16. The system according to claim 1, wherein the controller is arranged to adjust the field of view of the sensors automatically based on the location or absence of one or more identified feature or track component in the scan data relative to the field of view.

17. The system according to claim 2, wherein the actuator comprises a linear actuator and/or the support structure comprises one or more runner arranged to constrain motion of the track scanning sensors in unison to a single degree of freedom.

18. The system according to claim 3, wherein the track scanning sensors comprise at least two track scanning sensors mounted at spaced positions relative to the common support structure and opposingly oriented so as to scan a common railroad track component from opposing sides in use.

19. The system according to claim 2, wherein the visual imaging sensor comprises at least one digital image capture sensor and the track geometry measurement sensor comprises at least one depth detection sensor, wherein the depth detection sensor captures three-dimensional surface data of the one or more track components and the scan data processor automatically identifies features corresponding to the same one or more track components in both the three-dimensional surface data and the images from the digital image capture sensor.

20. The system according to claim 19, wherein the depth detection sensor captures three-dimensional surface data of the one or more track components and the scan data processor automatically identifies features corresponding to the same one or more track components in both the three-dimensional surface data and the images from the digital image capture sensor.

21. The system according to claim 3, further comprising a location determination system, the scan data processor arranged to index scan data with a location determination record corresponding to the location at which the scan data was obtained.

22. The system according to claim 21, wherein the location determination system comprises a vehicle travel distance sensor for determining the location of said sensor relative to a fixed datum point on the railroad track.

23. The system according to claim 22, wherein the vehicle travel distance sensor output is correlated with a location reading from a geographic coordinate determining system.

24. The system according to claim 2, wherein the scan data processor is arranged automatically to construct an image of a length of the railroad track from a plurality of consecutive scans from one or more of the track scanning sensors.

25. The system according to claim 1, wherein the scan data comprises one or more matrix of pixel intensity and/or color values and the scan data processor is arranged to identify features in said scan data by clustering pixels according to said intensity and/or color values.

26. The system according to claim 1, comprising:
a railroad vehicle travel sensor for sensing the speed, direction and/or travel distance of the railroad vehicle; and
a controller arranged to trigger a scan by the track scanning sensors according to an output of said vehicle travel sensor.

27. The system according to claim 26, wherein the vehicle travel sensor provides a pulsed output, the frequency of which corresponds to vehicle speed and a scan by the track scanning sensors is triggered by each pulse or a predetermined number of pulses.

28. The system according to claim 1, wherein the scan data processor comprises a plurality of processors, wherein at least one processor being arranged to log scan data captured by the plurality of track scanning sensors and associated location data in real time in the data store automatically upon receipt thereof.

29. The system according to claim 28, wherein at least one further processor is arranged to process the captured scan data automatically upon receipt thereof so as to identify track components in real-time or near-real-time.

30. The system according to claim 29, wherein at least one processor is arranged to perform analytical analysis of the scan data in order to identify a status or defect of the identified track components in real-time or near-real-time.

31. The system according to claim 1, wherein the data store comprises a non-volatile data store and a buffer for the scan data processor, the non-volatile data store comprising a database comprising raw scan data obtained from the sensors and a further database comprising track component classification and/or status data logged with a location record corresponding thereto.

32. The system according to claim 1, wherein the scan data processor determines a confidence score for a track component determination according to a degree of a match between a plurality of geometric and/or surface property features of a track component identified in the track scan data and one or more predetermined component features.

33. The system according to claim 1, comprising an alert module arranged to receive the output of the scan data processor and automatically determine whether one or more alert condition is met based on the one or more feature identified in said scan data.

34. The system according to claim 1, further comprising:
a data compression module.

35. The system according to claim 1 adapted for mounting to a passenger or freight revenue generating railway vehicle or locomotives in use.

36. The system according to claim 1, wherein the scan data processor or a further processor in communication therewith is arranged to output track component condition information derived from said track scan data, said track component condition information being provided as a track inspection report for use in planning track maintenance actions including track repair and/or renewal.

37. The system according to claim 36, wherein the track component condition information, including defect data with location information, is transmitted wirelessly from the vehicle to a central control or data centre from where end-users can retrieve it for further analysis and maintenance planning.

38. The system according to claim 2, further comprising:
a thermal imaging sensor used for component condition analysis.

39. The system according to claim 2, further comprising:
a position sensor working in combination with the visual imaging sensor and one or more track geometry measurement sensor system with analytics to measure rail parameters including position, orientation, profile wear, track gauge under both loaded and unloaded conditions, geometry parameters such as twist, super-elevation, curvature, and rail-wheel interface measurements such as the amount of hunting of wheel on the track.

40. The system according to claim 39, wherein the visual imaging capture sensor comprises a light sensor for sensing brightness and/or colour within a visible wavelength band.

41. The system according to claim 40, wherein the track scanning sensors comprise any combination of an areascan imaging sensor, a linescan imaging sensor, a three-dimensional surface profile sensor and an asset distance sensor.

42. The system according to claim 41, wherein the three-dimensional surface profile sensor and/or the asset distance sensor comprise a laser sensor device.

43. The system according to claim 2, wherein the visual imaging sensor is used with an asset/defect classifier and/or an asset/defect status analyser that correlates an asset feature in an image captured by one sensor with a corresponding image captured by one or more further sensor.

44. The system according to claim 43, wherein the asset feature comprises an edge profile and/or dimension of the asset and geometric feature or template matching is used to determine a degree of similarity between the feature of the detected asset and a predetermined geometric feature or template.

45. The system according to claim 43, wherein the asset feature comprises a surface property profile of the asset and surface property feature or template matching is used to determine a degree of similarity between the feature of the detected asset and a predetermined surface property feature or template.

46. The system according to claim 43, comprising a plurality of asset classifiers and an asset status analyser comprising two or more of a rule-based classifier, a template-based classifier and a statistical feature matching tool.

47. The system according to claim 1, wherein the scan data processor identifies one or more pixel clusters within an image according to one or more pixel brightness or colour property, each pixel clusters being used by an asset classifier and/or an asset status analyser used to determine an edge, colour, texture or shape feature of an asset which is used to determine its condition and position of defects.

48. The system according to claim 47, wherein the asset status analyser determines a change in asset orientation, shape, edge and/or color relative to a previously determined asset status characteristic.

49. The system according to claim 43, wherein the operation of the scan data processor comprising the asset classifier and/or asset status analyser is automated upon receipt of captured image data and/or location determination data.

50. The system according to claim 43, wherein the asset classifier and asset status analyser perform automated image analytics by use of software modules for processing image data to generate one or more output comprising the identity, properties and condition of each identified railroad track asset.

51. The system according to claim 1, further comprising:
a transmitter arranged to transmit a visual output signal to an operator console, the visual output signal comprising any or any combination of 2D or 3D maps indicating identified railroad track assets, asset risk reports, defects, and/or asset data graphs suitable for maintenance purposes.

52. The system according to claim 1,
wherein captured images from the track scanning sensors and location data from a location determining system are indexed by the scan data processor within one or more database in the data store.

53. The system according to claim 2, further comprising:
a linescan x-ray imaging sensor coupled with an x-ray source and used to image the inside of components such as rails, wherein such images are further processed with analytics software to diagnose internal flaws.

54. The system according to claim 1, wherein the track scanning sensors detect the accurate position of track rails in real-time and controls actuator movement to keep the position of sensors at the same relative position with respect to the rail when the vehicle is in motion, thus improving sensor analytics accuracy and measuring abnormal wheel hunting movement that can damage both the track rails and the wheel.

* * * * *